US011957702B2

(12) United States Patent
Willis et al.

(10) Patent No.: US 11,957,702 B2
(45) Date of Patent: *Apr. 16, 2024

(54) OPHTHALMIC SUSPENSION VEHICLES AND RELATED METHODS FOR PHARMACEUTICAL INGREDIENT DELIVERY

(71) Applicants: Timothy R Willis, Raleigh, NC (US); Ralph P. Stone, Fort Worth, TX (US)

(72) Inventors: Timothy R Willis, Raleigh, NC (US); Ralph P. Stone, Fort Worth, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/238,721

(22) Filed: Aug. 28, 2023

(65) Prior Publication Data

US 2023/0414646 A1  Dec. 28, 2023

Related U.S. Application Data

(63) Continuation of application No. 17/939,606, filed on Sep. 7, 2022, now Pat. No. 11,752,167, which is a continuation of application No. 17/689,219, filed on Mar. 8, 2022, now Pat. No. 11,471,475.

(51) Int. Cl.
| | |
|---|---|
| A61K 31/7076 | (2006.01) |
| A61K 9/00 | (2006.01) |
| A61K 9/10 | (2006.01) |
| A61K 47/02 | (2006.01) |
| A61K 47/06 | (2006.01) |
| A61K 47/36 | (2006.01) |
| A61K 47/44 | (2017.01) |

(52) U.S. Cl.
CPC ........ *A61K 31/7076* (2013.01); *A61K 9/0048* (2013.01); *A61K 9/10* (2013.01); *A61K 47/02* (2013.01); *A61K 47/06* (2013.01); *A61K 47/36* (2013.01); *A61K 47/44* (2013.01)

(58) Field of Classification Search
CPC .... A61K 31/7076; A61K 9/0048; A61K 9/10; A61K 47/02; A61K 47/06; A61K 47/36; A61K 47/44
See application file for complete search history.

(56) References Cited

U.S. PATENT DOCUMENTS

| | | |
|---|---|---|
| 4,151,001 A | 4/1979 | Anderson et al. |
| 4,421,748 A | 12/1983 | Trager et al. |
| 4,914,088 A | 4/1990 | Glonek et al. |
| 5,252,246 A | 10/1993 | Ding et al. |
| 5,278,151 A | 1/1994 | Korb et al. |
| 5,294,607 A | 3/1994 | Glonek et al. |
| 5,371,108 A | 12/1994 | Korb et al. |
| 5,578,586 A | 11/1996 | Glonek et al. |
| 5,672,358 A | 9/1997 | Tabibi |
| 5,756,449 A | 5/1998 | Andersen et al. |
| 5,942,558 A | 8/1999 | Korb et al. |
| 6,436,429 B1 | 8/2002 | Peyman |
| 8,591,033 B2 | 11/2013 | Korb et al. |
| 8,746,883 B2 | 6/2014 | Korb et al. |
| 8,915,592 B2 | 12/2014 | Korb et al. |
| 9,044,388 B2 | 6/2015 | Korb et al. |
| 9,161,905 B2 | 10/2015 | Korb et al. |
| 9,545,197 B2 | 1/2017 | Korb et al. |
| 2008/0091176 A1 | 4/2008 | Alessi et al. |
| 2008/0299206 A1 | 12/2008 | Lee et al. |
| 2010/0086512 A1 | 4/2010 | Schaefer |
| 2010/0247593 A1 | 9/2010 | Wikberg |
| 2012/0128763 A1 | 5/2012 | Maskin |
| 2013/0216596 A1 | 8/2013 | Viladot Petit |
| 2014/0206764 A1 | 7/2014 | Liu |
| 2014/0329843 A1 | 11/2014 | Richardson et al. |
| 2015/0174067 A1 | 6/2015 | Sun et al. |
| 2015/0202306 A1 | 7/2015 | Coffey |
| 2015/0297511 A1 | 10/2015 | Xia |
| 2016/0199428 A1 | 7/2016 | Simmons et al. |
| 2016/0338952 A1 | 11/2016 | Ketelson |
| 2016/0354307 A1 | 12/2016 | Hilliard |
| 2018/0008538 A1 | 1/2018 | Izquierdo Torres |
| 2018/0325854 A1 | 11/2018 | Coulon |
| 2019/0022231 A1 | 1/2019 | Rabinovich-Guilatt et al. |
| 2020/0179281 A1 | 6/2020 | Willis et al. |
| 2021/0145739 A1 | 5/2021 | Perry et al. |
| 2021/0196628 A1 | 7/2021 | Ketelson et al. |

FOREIGN PATENT DOCUMENTS

| | | |
|---|---|---|
| EP | 0 459 148 A2 | 12/1991 |
| EP | 0 535 545 | 7/1993 |
| WO | 2006004577 A2 | 1/2006 |
| WO | 2014035451 A1 | 3/2014 |
| WO | 2015055301 A1 | 4/2015 |
| WO | 2017074420 A1 | 5/2017 |
| WO | 2017132190 A1 | 8/2017 |

OTHER PUBLICATIONS

International Search Report for PCT/US2019/065191, dated Mar. 19, 2020.
Wikipedia Contributors, "Beeswax," Wikipedia, accessed Sep. 27, 2018. Available at https://en.wikipedia.org/w/index.php?title=Beeswax &oldid=861444220, 7 pages.
Wikipedia Contributors, "Eye Drop," Wikipedia, accessed Sep. 13, 2018. Available at https://en.wikipedia.org/w/index.php?title=Beeswax &oldid=847772327, 4 pages.
Wikipedia Contributors, "Surfactant," Wikipedia, accessed Sep. 13, 2018, 11:50 UTC. Available at https://en.wikipedia.org/w/index. php?title=Beeswax&oldid=858602819, 11 pages.
Freeman, P. David, and Kahook, Malik Y. "Preservatives in Topical Ophthalmic Medications: Historical and Clinical Perspectives." Expert Rev Ophthalmol. 2009;4(1):59-64. Expert Reviews Ltd., London.

(Continued)

*Primary Examiner* — Jonathan S Lau
(74) *Attorney, Agent, or Firm* — Barnes & Thornburg LLP

(57) ABSTRACT

This disclosure is directed to ophthalmic suspension vehicles for delivery of at least one pharmaceutical ingredient to a patient in need of treatment. The disclosure also provides methods of delivering at least one pharmaceutical ingredient to a patient in need of treatment.

20 Claims, 1 Drawing Sheet

(56) References Cited

OTHER PUBLICATIONS

Klier, John. "Microemulsions." In Kirk-Othmer Encyclopedia of Chemical Technology, John Wiley & Sons, Inc (Ed.), United States, dated Jul. 13, 2012, 22 pages.

Korb, Donald R. "Survey of Preferred Tests for Diagnosis of Tear Film and Dry Eye." Cornea, 19(4): 483-486 (2000), Lippincott Williams and Wilkins, Inc., Philadelphia.

Kostansek, Edward. "Emulsions." In Kirk-Othmer Encyclopedia of Chemical Technology, John Wiley & Sons, Inc (Ed.), United States, dated Jul. 12, 2012, 24 pages.

Lanigan, Rebecca S., and Yamarik, Torrill A. "Final Report on the Safety Assessment of PEG-6, -8, and -20 Sorbitan Beeswax." Int. J. Toxicology, 20(Supp. 4):27-38 (2001). Cosmetic Ingredient Review Panel, SAGE Publishing, United States.

Leray, Claude. "Waxes." In Kirk-Othmer Encyclopedia of Chemical Technology, John Wiley & Sons, Inc (Ed.), United States, dated Sep. 15, 2016, 25 pages.

Moshirfar, Majid et al. "Artificial tears potpourri: A literature review." Clinical Ophthalmology, vol. 2014 (8):1419-1433 (2014), Dove Press, United States.

Patel, Ashaben et al. "Ocular drug deliver systems: An overview." World J Pharmacol., 2(2): 47-64 (2013). Baishideng Publishing Group Inc, United States.

Pucker, AD, NG, SM, and Nichols, JJ. "Over the counter (OTC) artificial tear drops for dry eye syndrome." Cochrane Database of Systematic Reviews, Issue 2. Art. No. CD009729 (2016). John Wiley & Sons, Ltd., United States.

Restasis MultiDose TM [product prescribing information]. Irvine, CA: Allergan; revised Oct. 2016.

Sweeney, Deborah F., et al. "Tear film stability: A review." Experimental Eye Research, 117, 28-38 (2013). Elsevier Ltd., United States.

Tadros, Tharwat. "Surfactants." In Kirk-Othmer Encyclopedia of Chemical Technology, John Wiley & Sons, Inc (Ed.), United States, dated Jul. 13, 2012, 46 pages.

Fisher Chemical—Fisher Scientific, product listing for "Mineral Oil, Light (NF/FCC), Fisher Chemical", [online] https://www.fishersci.com/shop/products/mineral-oil-light-nf-fcc-fisher-chemical-3/O1211 (Accessed May 13, 2021).

Fisher Chemical—Fisher Scientific, product listing for "Mineral Oil, Heavy (USP/FCC), Fisher Chemical", [online] https://www.fishersci.com/shop/products/mineral-oil-light-nf-fcc-fisher-chemical-2/O1211 (Accessed May 13, 2021).

Tamilvanan, S., et al., "The potential of lipid emulsion for ocular delivery of lipophilic drugs", European Journal of Pharmaceutics and Biopharmaceutics, (2004), vol. 58, pp. 357-368.

Stahl et al., Clinical and Experimental Optometry, 2012, 95(1), p. 3-11. (Year: 2012).

Office Action dated Oct. 13, 2022, issued in U.S. Appl. No. 17/854,680.

Vogel, et al., "Drug Discovery and Evaluation: Methods in Clinical Pharmacology", Springer-Verlag Berlin Heidelberg, (2011), pp. 1-40.

Office Action dated Jan. 26, 2023, issued in U.S. Appl. No. 17/854,680.

Vo, et al., "Factors affecting the particle size distribution and rheology of brinzolamide ophthalmic suspensions", International Journal of Pharmaceutics, 586, article 119495, (2020), 11 pages.

International Search Report for PCT/US2022/042727, dated Jan. 31, 2023.

DRAKEOL 15 LT MIN OIL,NF. Datasheet [online], Calumet Specialty Products Partners, L.P., 2014 [retrieved on Nov. 11, 2022] Retrieved from the Internet: <URL: http://glenncorp.com/wp-content/uploads/2017/03/Dr-15-DR-TDS.pdf>.

DRAKEOL 35 MIN OIL USP. Datasheet [online], Calumet Specialty Products Partners, L.P., 2014 [retrieved on Nov. 11, 2022] Retrieved from the Internet: <URL: http://glenncorp.com/wp-content/uploads/2017 /03/Drakeol-35-Min-O11-USP .-Spec.-06.24.14.pdf>.

Honary et al., Tropical Journal of Pharmaceutical Research, 2013, 12(2), p. 265-273. (Year: 2013).

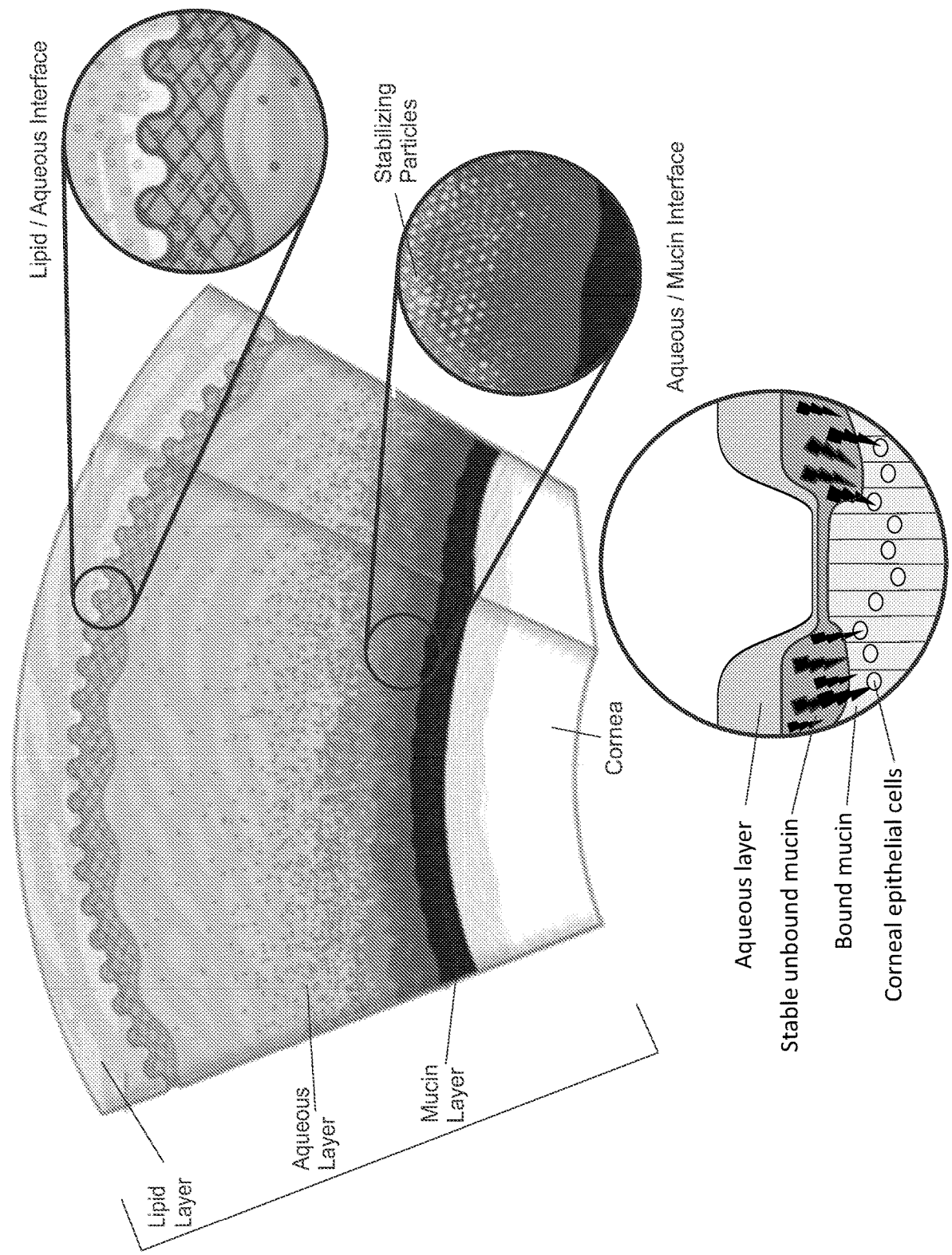

OPHTHALMIC SUSPENSION VEHICLES AND RELATED METHODS FOR PHARMACEUTICAL INGREDIENT DELIVERY

CROSS REFERENCE TO RELATED APPLICATION

This application is continuation of U.S. application Ser. No. 17/939,606, filed Sep. 7, 2022, which is a continuation of U.S. application Ser. No. 17/689,219, filed Mar. 8, 2022, now U.S. Pat. No. 11,471,475 issued Oct. 18, 2022, the contents of which are each hereby incorporated by reference.

FIELD

The present disclosure provides ophthalmic suspension vehicles for the delivery of a long lasting ocular therapy to the eye. Particularly, the ophthalmic suspension vehicles described herein provide long lasting delivery of pharmaceutical ingredients to the eye for an extended time.

BACKGROUND

Long lasting release of therapeutic drugs onto the eye has been attempted over the last 25 years. This has been attempted with both ophthalmic pharmaceutical formulations and devices for drug delivery to provide for the release of an active therapeutic ingredient or drug with resultant effect to the eye. Unfortunately, consistent delivery over time on the eye with a pharmaceutical formulation has not been achieved because ophthalmic formulations, to date, and their vehicles only remain on the eye from 5 minutes to 30 minutes maximum. Thus, an ideal delivery vehicle for active drug with requirements to remain on the eye for an extended time beyond 30 minutes has not been possible. Such a shortcoming is partially based on the fact that the tear film produced by secretions of the different glands of the eye during normal blinking causes the pharmaceutical ingredient and vehicle to drain from the eye. The largest portion of the tear film is the aqueous of the tear and is produced by primarily the lacrimal gland activated by blinking. The external tear film layer is the lipid layer which is excreted during blinking primarily from the Meibomian glands located in the eye lids. The lipid layer provides a protective layer on top of the tear film designed to reduce the evaporation of the aqueous of the tear film. Thinning of the lipid layer adds increased evaporation of the aqueous layer resulting in a dry eye on the corneal surface between blinks. Such dry eye patients' tear film rate of evaporation increases by 30% to 38% at less than 50% relative humidity. This is in addition to the measured loss of the aqueous layer through the punta. These collective secretions from the lacrimal and Meibomian glands along with eye lid providing a wiper effect from normal blinking provides a normal, long lasting, and stable ocular tear film. While the normal production of ingredients continually repair and replace the tear film, the loss of key ingredients due to dysfunction or non-secretions makes the tear film unstable and rapidly leads to loss of the tear film structure resulting in dry eye. The dry eye issues caused by a dysfunctional tear film results in vehicles and drug actives to not stay on the eye for long periods of time.

Normal tears with the correct balance of lipid, aqueous and mucin components combined during blinking form a stable and protective tear film. Between blinks, the tear film thins due to evaporation and lipid molecules from the outer layer begin to migrate through the aqueous layer towards the mucin layer. The aqueous portion of the tear also is exchanged on the eye by approximately 16% by volume every minute where the lipid layer is exchanged at a rate of approximately 2% per minute on the eye. Contamination of the mucin layer by the lipid layer increases the surface tension of the tear film and eventually causes it to rupture (break-up) and bead up on the surface of the cornea forming a dry spot. A subsequent blink normally repairs this rupture by removing the lipid contaminants from the mucin layer and restoring a normal aqueous layer. Repeated rupture, however, can cause loss of the mucin layer and show staining when observed using fluorescein.

U.S. Pat. Nos. 5,371,108, 5,278,151 and U.S. Patent Publication No 2016/03389952 to Korb teach a method or formulation for creating an emulsion or gel comprising oil and wax to form a tear film on the ocular surface to prolong the residence time of oil. The wax-containing gel has not, however, been produced and marketed commercially because of the difficulty in homogenizing the wax in such a way that does not induce visual blurring beyond what would be acceptable by most consumers. Specifically, autoclaving to sterilize the wax-containing formulation leads to increased particle size which leads to irritation and blurred vision. Gels are semi-solid formulations with high viscosity. In contrast, the present disclosure is directed to metastable emulsions that behave as flowing liquids at room temperature. Emulsions behave as liquids and as such do not exhibit a static internal structure or have high viscosity. Korb also utilizes preservatives at levels that are known to be toxic to cornea cells upon administration and does not disclose a vehicle that would exhibit a long lasting dwell time A number of ophthalmic formulations and compositions of use note the use of Zeta potential and are disclosed in WO2016209555, WO2015057847, WO2011098578, WO2011084509, WO03053405, US2012328702, US2012225834, and U.S. Pat. Nos. 7,060,285, 9,827,191, 8,298,569, 7,893,040, 7,834,172, and 10,137,083 each incorporated herein by reference for its teaching of the use of Zeta potential.

The tear film can be used as a base to provide ocular delivery of pharmaceutical ingredients in small concentrations has been a challenge to industry. See Patel et al. 2013, "Ocular drug delivery systems: An overview" World J. Pharmacol 2(2) 47-64. An acceptable carrier of pharmaceutical ingredients needs to mimic the properties and osmolarity of the natural tear film and remain on the eye for an extended period of time. Such a product would increase the bioavailability of the active pharmaceutical ingredient ("API") to the corneal epithelial cells, a long desired pathway for ocular drugs.

SUMMARY OF THE DISCLOSURE

Disclosed herein are ophthalmic suspensions that include ophthalmic suspension vehicles that are useful for delivering at least one pharmaceutical ingredient to an eye's ocular surface. The ophthalmic suspensions enable enhanced bioavailability by delivering at least one pharmaceutical ingredient to an eye's ocular surface. The ophthalmic suspension's dwell time on the eye allows for prolonged and improved delivery of at least one pharmaceutical ingredient to the eye thereby by resulting in increased contact time of the at least one pharmaceutical ingredient on the eye. The ophthalmic suspension's dwell time on the eye also allow for lower levels of pharmaceutical ingredient to be utilized while achieving the required therapeutic effect while reducing any unwanted side effects.

Methods for delivering at least one pharmaceutical ingredient to a patient in need of treatment are also provided. The method includes the step of administering to an eye of the patient, an ophthalmic suspension as provided herein.

BRIEF DESCRIPTION OF THE FIGURES

FIG. 1 shows an enlarged view of the tear film identifying different regions. The normal tear film is 3-6 microns thick. The FIGURE shows the lipid layer, the lipid/aqueous interface, the aqueous layer, the aqueous/mucin interface, the mucin layer, and the cornea. Two of the insets show enlarged views of the lipid/aqueous interface and the aqueous/mucin interface. The third inset shows the thinning of the layers and interfaces associated with dry eye. In particular, the third inset shows the thinning of (i) the aqueous layer, (ii) the unbound mucin layer, and (iii) the bound mucin layer which is bound the surface of the corneal epithelial cells. Methodologies to evaluate tear film are further provided in U.S. Ser. No. 16/708,120 (U.S. Pub. No. 2020/0179281), the entire contents of which are incorporated herein by reference.

DETAILED DESCRIPTION OF THE DISCLOSURE

While the following terms are believed to be well understood by one of ordinary skill in the art, the following definitions are set forth to facilitate explanation of the presently disclosed subject matter.

As used herein, the term "pharmaceutical ingredient" refers to a substance used in a finished pharmaceutical product (FPP), intended to furnish pharmacological activity or to otherwise have direct effect in the diagnosis, cure, mitigation, treatment or prevention of disease or disorder, or to have direct effect in restoring, correcting or modifying physiological functions in human beings.

As used herein, the terms "about" and/or "approximately" may be used in conjunction with numerical values and/or ranges. The term "about" is understood to mean those values near to a recited value. Alternatively, depending on the context, the term "about" may mean±one half a standard deviation, one standard deviation, or ±two standard deviations. Furthermore, the phrases "less than about [a value]" or "greater than about [a value]" should be understood in view of the definition of the term "about" provided herein. The terms "about" and "approximately" may be used interchangeably. Throughout the present specification, numerical ranges are provided for certain quantities.

As used herein, the verb "comprise" as used in this description and in the claims and its conjugations are used in its non-limiting sense to mean that items following the word are included, but items not specifically mentioned are not excluded.

As used herein, the word "comprising," or variations such as "comprises" or "comprising," will be understood to imply the inclusion of a stated element, integer or step, or group of elements, integers or steps, but not the exclusion of any other element, integer or step, or group of elements, integers or steps. The present disclosure may suitably "comprise", "consist of", or "consist essentially of", the steps, elements, and/or reagents described in the claims.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

As used herein, the term "percent weight" refers to the amount based on the ophthalmic suspension vehicle, unless noted otherwise.

As used herein, the term "wax ester" refers to an ester of a fatty acid and a fatty alcohol and may include a number of compounds with a variety of carbon chain lengths. The wax esters provided herein may include long carbon chains. The wax esters provided herein may be present in solid particles that exhibit a melting point of from about 60° C. to about 100° C. The wax esters provided herein may be natural beeswax. Natural beeswax is also commercially available as *Cera Alba* or *Cera Flava* (White or Yellow Beeswax). The use of natural beeswax may include a hydrocarbon as a component. During the preparation of one embodiment of an emulsion of the present disclosure, the wax esters may hydrolyze forming additional acids and/or alcohols as part of the process. The terms "wax ester dispersion" and "wax dispersion" may be used interchangeably.

As used herein, the term "particle size" refers to the size of wax ester particles alone, or in combination with, one or more oil, phospholipid, surfactant, hyaluronic acid (HA), sodium hyaluronate, or any other ophthalmic suspension vehicle component provided herein.

As used herein, the term "dwell time" refers to the time (e.g., minutes or hours) that an ophthalmic suspension vehicle remains on the eye from one application when evaluating the level or amount of lipid layer thickness from a baseline on the eye. Lipid layer thickness can be determined by interferometry instrumentation to measure dwell time on the eye.

As used herein, the term "long lasting" refers to the increase in the dwell time observed over a period of time and demonstrated compared to an untreated eye.

As used herein, the term "stable" refers to the time the tear film maintains structure between blinks.

As used herein, the term "tear film" refers to the entire protective coating provided to the eye, including that illustrated in FIG. 1.

As used herein, the term "dry eye" refers to a condition of the eye where the tear film is unable to perform its function of lubrication and may be caused by a lack of critical components to form a stable tear film.

As used herein, the term "dry delivery" refers to the use of the ophthalmic suspension vehicles provided herein to provide sustained release of at least one pharmaceutical ingredient to the ocular surface over an extended period of time.

As used herein, the terms "light mineral oil" and "light weight mineral oil" may be used interchangeably and refer to a low viscosity mineral oil as defined in the NF or USP formulary.

As used herein, the terms "heavy mineral oil" and "heavy weight mineral oil" may be used interchangeably and refer to a high viscosity mineral oil variant that meets the requirements of the NF or USP monographs for mineral oil.

Unless defined otherwise, all technical and scientific terms used herein have the same meanings as commonly understood by one of ordinary skill in the art to which this disclosure belongs.

The present disclosure relates to ophthalmic suspensions and related methods. The ophthalmic suspensions provided herein include an ophthalmic suspension vehicle and at least one pharmaceutical ingredient that is added to provide long lasting delivery of the active pharmaceutical upon delivery to a patient's eye.

The ophthalmic suspensions vehicles include an aqueous phase and an oil phase. The aqueous phase may include water and one or more at least one wax ester, at least one anionic polar surfactant, at least one nonionic surfactant, at least one salt and at least one phosphate. The water utilized in the ophthalmic suspension vehicles provided herein may be purified or deionized water. The oil phase may include at least one mineral oil and, optionally, at least one wax ester. Thus, the at least one wax ester may be present in the aqueous phase, the oil phase, or both the aqueous phase and oil phase. According to a particular embodiment, the at least one wax ester is in either the aqueous phase or oil phase.

The ophthalmic suspensions provided herein include at least one pharmaceutical ingredient. The ophthalmic suspensions provide delivery of the at least one pharmaceutical ingredient such that the at least one pharmaceutical ingredient is maintained within the ophthalmic suspension vehicle and in therapeutic contact with the eye for at least two hours after administering to the eye. According to one embodiment, the at least one pharmaceutical ingredient is soluble in the aqueous phase. According to another embodiment, the at least one pharmaceutical ingredient is soluble in the oil phase.

The at least one oil present in the ophthalmic suspension vehicles provided herein may be derived from animals, plants, nuts, or other suitable sources. The oil derived from animals, plant seeds, and nuts are similar to fats and are primarily glycerides or fatty acids and consequently, contain a significant number of acid and/or ester groups rendering the oil polar. Examples of these oils are safflower oil, corn oil, canola oil, whale oil and seal oil or chemically similar oils. Additional oils as provided herein include a vegetable oil such as a castor oil, almond oil, myrcia oil, corn oil, peanut oil, canola oil, safflower oil, kola nut oil, light olive oil, bay leaf oil, or other generally recognized as safe (GRAS) oils listed as being appropriate for ocular formulation. Alternatively, the oil may be an oil suited for forming liposomes. According to one embodiment, the oil is a linear hydrocarbon oil having from 10 to 150 carbon atoms and, more preferably, the oil is a saturated n-alkane or isoalkane hydrocarbon having from 10 to 26 carbon atoms. Unsaturated alkene hydrocarbons may be used but are less chemically stable.

According to one embodiment, the oil present in the ophthalmic suspension vehicles provided herein is a mineral oil. According to one embodiment, the oil as provided herein is a lightweight mineral oil. According to one embodiment, the oil as provided herein is a heavy weight mineral oil.

According to one embodiment, the oil present in the ophthalmic suspension vehicles provided herein includes a mixture of light weight mineral oil and heavy weight mineral oil each having differing viscosities. According to a particular embodiment, the lightweight mineral oil exhibits a kinetic viscosity of from about 3.0 $mm^2s^{-1}$ to about 34.4 $mm^2s^{-1}$ at 40° C. According to a particular embodiment, the heavy weight mineral oil exhibits a viscosity of kinetic viscosity of from about 34.5 $mm^2s^{-1}$ to about 150 $mm^2s^{-1}$ at 40° C. According to yet another embodiment, the lightweight mineral oil exhibits a kinetic viscosity of from about 28 $mm^2s^{-1}$ to about 30 $mm^2s^{-1}$ at 40° C. According to yet another embodiment, the heavy weight mineral oil exhibits a viscosity of kinetic viscosity of from about 65 $mm^2s^{-1}$ to about 71 $mm^2s^{-1}$ at 40° C.

The amount of oil within the oil phase may vary within reasonable limits, however, application to the eye should not exceed 25 µL. According to one embodiment, the volume does not exceed 15 µL. According to one embodiment, the volume varies between about 1 µL and 10 µL. According to one embodiment, the volume varies between about 1 µL and 30 µL.

The total amount of oil or combination of oils may be present in the ophthalmic suspension vehicles in an amount of at least about 0.1 percent by weight based on the total weight of the ophthalmic suspension vehicle. According to one embodiment, the oil or combination of oils is present in an amount of at least about 0.5 percent by weight. According to one embodiment, the oil or combination of oils is present in an amount of at least about 1.0 percent by weight. According to one embodiment, the oil or combination of oils is present in an amount of at least about 1.5 percent by weight. According to one embodiment, the oil or combination of oils is present in an amount of less than about 12.5 percent by weight. According to one embodiment, the oil or combination of oils is present in an amount of less than about 10.0 percent by weight. According to one embodiment, the oil or combination of oils is present in an amount of less than about 7.5 percent by weight. According to one embodiment, the oil or combination of oils is present in an amount of less than about 6.6 percent by weight. According to one embodiment, the oil or combination of oils is present in an amount of less than about 6.5 percent by weight. According to one embodiment, the oil or combination of oils is present in an amount of between about 0.5 percent by weight and about 12.5 percent by weight. According to one embodiment, the oil or combination of oils is present in an amount of between about 1.0 percent by weight and about 8.5 percent by weight. According to one embodiment, the oil or combination of oils is present in an amount of between about 3.5 percent by weight and about 7.5 percent by weight. According to one embodiment, the oil or combination of oils is present in an amount of between about 4.0 percent by weight and about 7.0 percent by weight. According to one embodiment, the oil or combination of oils is present in an amount of between about 4.4 percent by weight and about 6.6 percent by weight. According to one embodiment, the oil or combination of oils is present in an amount of between about 4.95 percent by weight and about 6.05 percent by weight.

According to one embodiment, the oil present in the ophthalmic suspension vehicles provided herein includes a mixture of two or more oils of differing weight. According to such an embodiment, the oil is a mixture of at least one light weight oil and at least one heavy weight oil. According to a particular embodiment, the oil is a mixture of the mineral oils marketed under the tradenames Drakeol® 15 (light weight mineral oil) and Drakeol® 35 (white, heavy mineral oil). According to one embodiment, the lightweight mineral oil may be present in an amount of from about 0.5 percent by weight to about 1.5 percent by weight. According to one embodiment, the lightweight mineral oil may be present in an amount of from about 0.6 percent by weight to about 1.4 percent by weight. According to one embodiment, the lightweight mineral oil may be present in an amount of from about 0.7 percent by weight to about 1.3 percent by weight. According to one embodiment, the lightweight mineral oil may be present in an amount of from about 0.8 percent by weight to about 1.2 percent by weight.

According to one embodiment, the heavy weight mineral oil may be present in an amount of from about 2.7 percent by weight to about 6.5 percent by weight. According to one embodiment, the heavy weight mineral oil may be present in an amount of from about 2.9 percent by weight to about 6.3 percent by weight. According to one embodiment, the heavy weight mineral oil may be present in an amount of from about 3.1 percent by weight to about 6.1 percent by weight. According to one embodiment, the heavy weight mineral oil may be present in an amount of from about 3.3 percent by weight to about 5.9 percent by weight. According to one embodiment, the heavy weight mineral oil may be present in an amount of from about 3.5 percent by weight to about 5.7 percent by weight. According to one embodiment, the heavy weight mineral oil may be present in an amount of from about 3.7 percent by weight to about 5.5 percent by weight. According to one embodiment, the heavy weight mineral oil may be present in an amount of from about 4.05 percent by weight to about 4.95 percent by weight.

According to one embodiment, the lightweight mineral oil may be present in an amount of about 1.0 percent by weight and the heavy weight mineral oil may be present in an amount of about 4.5 percent by weight.

The ophthalmic suspension vehicles provided herein include at least one wax ester. While not being bound to a particular theory, the role of wax esters and their hydrolysis products is believed to maintain the integrity of the interstitial layers themselves, binding the mucin layer to the aqueous layer and aqueous layer to the lipid layer. In addition, the wax esters serve to build up an thicken the mucin, the aqueous layer, and the lipid layer themselves. The binding process and subsequent homeostasis enabled by the wax esters allows the layers of the tear film to cling to each other, thus allowing the entire tear film to remain on the eye for extended periods of time and provide drug delivery of at least one pharmaceutical ingredient. The ophthalmic suspension vehicles provided herein penetrate all layers of the tear film including the interstitial layers of which no product has incorporated previously.

According to one embodiment, the wax ester is insoluble thereby providing an ophthalmic suspension that is slowly dissolved in the presence of the wax esters that are secreted by the glands of the eye, thereby increasing the viscosity of the lipid layer. This has the effect of actually slowing the tear film turnover rate through the puncta, as a higher viscosity liquid will flow more slowly than the unstable and low-viscosity tear film of a dry eye patient.

According to one embodiment, the at least one wax ester is present in the ophthalmic suspension vehicle in an amount of at least about 0.2 weight percent. According to one embodiment, the at least one wax ester is present in an amount of at least about 0.3 weight percent. According to one embodiment, the at least one wax ester is present in an amount of at least about 0.4 weight percent. According to one embodiment, the at least one wax ester is present in an amount of at least about 0.5 weight percent. According to one embodiment, the at least one wax ester is present in an amount of at least about 0.6 weight percent. According to one embodiment, the at least one wax ester is present in an amount of at least about 0.7 weight percent. According to one embodiment, the at least one wax ester is present in an amount of at least about 0.8 weight percent. According to one embodiment, the at least one wax ester is present in an amount of at least about 0.9 weight percent. According to one embodiment, the at least one wax ester is present in an amount of at least about 1.0 weight percent. According to one embodiment, the at least one wax ester is present in an amount of less than about 1.8 weight percent. According to one embodiment, the at least one wax ester is present in an amount of from about 0.2 weight percent to about 1.8 weight percent. According to one embodiment, the at least one wax ester is present in an amount of from about 0.4 weight percent to about 1.6 weight percent. According to one embodiment, the at least one wax ester is present in an amount of from about 0.6 weight percent to about 1.4 weight percent. According to one embodiment, the at least one wax ester is present in an amount of from about 0.8 weight percent to about 1.2 weight percent. According to one embodiment, the at least one wax ester is present in an amount of about 1.0 weight percent.

According to one embodiment, the at least one wax ester is a beeswax. According to one embodiment, the beeswax is a natural beeswax. The beeswax may be *Cera Alba, Cera Flava*, or a combination thereof. The beeswax may be USDA Certified Organic beeswax or conventional natural beeswax. According to one embodiment, at least one wax ester is a synthetic beeswax.

The ophthalmic suspension vehicles provided herein include wax ester particles. According to one embodiment, the wax or wax ester particles may be mixed with at least one oil as provided herein. According to one embodiment, the wax or wax ester particles may be mixed with water and at least one oil as provided herein.

According to one embodiment, the wax ester particles as provided herein exhibit a particle size that allows the particle to be retained on and in contact with the eye to allow for delivery of at least one pharmaceutical ingredient. According to one embodiment, the wax ester particles as provided herein form an emulsion particle that is retained on and in contact with the eye to allow for delivery of at least one pharmaceutical ingredient.

According to one embodiment, the wax ester particles may be emulsified into the ophthalmic suspension vehicles to form a range of specific particle sizes. The irregular shape and charge of the particles themselves allow the wax ester particles more surface area to interact with the oil as provided herein and allows the wax ester particles to break down at a varied rate, with the smaller wax ester particles and oil particles breaking down quickly, and the larger wax ester particles breaking down more slowly. As wax ester particles are broken down, the oil and wax esters particles are believed to interact with the natural tear film to support a more stable barrier for the evaporation-prone aqueous tear film.

According to one embodiment, the wax ester particles exhibit a mean particle size of at least about 2.0 microns. According to one embodiment, the wax ester particles exhibit a mean particle size of at least about 3.0 microns. According to one embodiment, the wax ester particles exhibit a mean particle size of at least about 4.0 microns. According to one embodiment, the wax ester particles exhibit a mean particle size of at least about 5.0 microns. According to one embodiment, the wax ester particles exhibit a mean particle size of less than about 30.0 microns. According to one embodiment, the wax ester particles exhibit a mean particle size of less than about 25.0 microns. According to one embodiment, the wax ester particles exhibit a mean particle size of less than about 24.0 microns. According to one embodiment, the wax ester particles exhibit a mean particle size of less than about 23.0 microns. According to one embodiment, the wax ester particles exhibit a mean particle size of less than about 22.0 microns. According to one embodiment, the wax ester particles exhibit a mean particle size of less than about 21.0 microns. According to one embodiment, the wax ester particles exhibit a mean particle size of less than about 20.0 microns. According to one embodiment, the wax ester particles exhibit a mean particle size of at least about 2.0 microns but less than about 25.0 microns. According to one embodiment, the wax ester particles exhibit a mean particle size of at least about 2.0 microns but less than about 20.0 microns. According to one embodiment, the wax ester particles exhibit a mean particle size of at least about 2.0 microns but less than about 15.0 microns. According to one embodiment, the wax ester particles exhibit a mean particle size of at least about 3.0 microns but less than about 24.0 microns. According to one embodiment, the wax ester particles exhibit a mean particle size of at least about 4.0 microns but less than about 23.0 microns. According to one embodiment, the wax ester particles exhibit a mean particle size of at least about 5.0 microns but less than about 22.0 microns. According to one embodiment, the wax ester particles exhibit a mean particle size of at least about 6.0 microns but less than about 21.0 microns. According to one embodiment, the wax ester particles exhibit a mean particle size of at least about 7.0 microns but less than about 20.0 microns. According to one embodiment, the wax ester particles exhibit a mean particle size of at least about 10.0 microns but less than about 15.0 microns.

The ophthalmic suspension vehicles provided herein include at least one surfactant. According to one embodiment, the ophthalmic suspension vehicle includes at least two or more surfactants. According to one embodiment, the ophthalmic suspension vehicles include a combination of surfactants for the dual purpose of stabilizing the vehicle and the at least one pharmaceutical ingredient, as well as spreading and maintaining the vehicle and pharmaceutical ingredient over the ocular surface following application to the eye. In one embodiment, the surfactant combination may include a primary surfactant and secondary surfactant. The at least one surfactant enables formation of an ophthalmic suspension vehicle that is stable in manufacture and during storage, but desirably meta stable when applied to the ocular surface. As one example, when applied to the ocular surface, the at least one surfactant allows for a phase separation of components. The at least one surfactant as provided herein is suitable for rapid differentiation when applied to the eye whereby a non-blurring film of oil is rapidly formed over the ocular surface and disseminates the wax ester through each phase of the ophthalmic suspension vehicle.

According to one embodiment, the at least one surfactant includes at least one polyoxyethylene sorbitan monooleate such as polyoxyethylene-sorbitan-20 mono-oleate which is commercially available as Polysorbate 80 or Tween 80. According to one embodiment, the polyoxyethylene sorbitan monooleate may be present in the ophthalmic suspension vehicle in an amount of from about 0.1 percent weight to about 0.7 percent weight. According to one embodiment, the polyoxyethylene sorbitan monooleate may be present in the ophthalmic suspension vehicle in an amount of from about 0.2 percent weight to about 0.6 percent weight. According to one embodiment, the polyoxyethylene sorbitan monooleate may be present in the ophthalmic suspension vehicle in an amount of from about 0.3 percent weight to about 0.6 percent weight. According to one embodiment, the polyoxyethylene sorbitan monooleate may be present in the ophthalmic suspension vehicle in an amount of from about 0.4 percent weight to about 0.6 percent weight.

According to one embodiment, the at least one surfactant includes diphosphatidylglycerol such as dimyristoylphosphatidylglycerol or 1,2-Dimyristoyl-sn-glycero-3-phosphorylglycerol sodium salt (DMPG) which is commercially available. The surfactant may be a lysophosphatidylcholine, a phosphatidic acid, a phosphatidylcholine, a phosphatidylethanolamine, a phosphatidylglycerol, or a phosphatidylserine. In other embodiments, the surfactant includes at least one anionic surfactant. According to one embodiment, the anionic surfactant may be one or more of an anionic polar phospholipid, such as a lysophosphatidylcholine, a phosphatidic acid, a phosphatidylcholine, a phosphatidylethanolamine, a phosphatidylglycerol, or a phosphatidylserine. According to another embodiment, the anionic polar phospholipid may be one or more of phosphatidic acid (PA), phosphatidylserine (PS), phosphatidylinositol (PI), and its phosphorylated derivatives the phosphoinositides (e.g. phosphatidylinositol-4-phosphate [PI4P] and phosphatidylinositol-4,5-bisphosphate, also dimyristoylphopatidyl glycerol. According to one embodiment, the anionic surfactant is a dimyristoylphosphatidylglycerol. According to one embodiment, the surfactant is a mixture of two surfactants as provided herein. According to one embodiment, the surfactant is a combination of two anionic polar phospholipids. According to one embodiment, the anionic polar surfactant is a mixture of a Tween 80 and anionic polar dimyristoylphosphatidylglycerol.

According to one embodiment, the dimyristoylphosphatidylglycerol may be present in the ophthalmic suspension vehicle in an amount of from about 0.1 percent weight to about 0.7 percent weight. According to one embodiment, the dimyristoylphosphatidylglycerol may be present in the ophthalmic suspension vehicle in an amount of from about 0.2 percent weight to about 0.6 percent weight. According to one embodiment, the dimyristoylphosphatidylglycerol may be present in the ophthalmic suspension vehicle in an amount of from about 0.3 percent weight to about 0.6 percent weight. According to one embodiment, the dimyristoylphosphatidylglycerol may be present in the ophthalmic suspension vehicle in an amount of from about 0.4 percent weight to about 0.6 percent weight.

According to one embodiment, the ophthalmic suspension vehicles provided herein include one or more phosphates. According to one embodiment, the ophthalmic suspension vehicles include both a monobasic and a dibasic phosphate.

According to a particular embodiment, the monobasic phosphate is monosodium phosphate (monobasic sodium phosphate) such as $NaH_2PO_4$. According to one embodiment, the monobasic phosphate may be present in an amount of from about 0.01 percent by weight to about 0.05 percent by weight. According to one embodiment, the monobasic phosphate may be present in an amount of from about 0.02 percent by weight to about 0.04 percent by weight. According to one embodiment, the monobasic phosphate may be present in an amount of about 0.03 percent by weight.

According to a particular embodiment, the dibasic phosphate is disodium phosphate (sodium hydrogen phosphate or sodium phosphate dibasic) such as $Na_2HPO_4$. According to one embodiment, the dibasic phosphate may be present in an amount of from about 0.1 percent by weight to about 0.5 percent by weight. According to one embodiment, the dibasic phosphate may be present in an amount of from about 0.2 percent by weight to about 0.3 percent by weight. According to one embodiment, the dibasic phosphate may be present in an amount of about 0.25 percent by weight.

According to one embodiment, the ophthalmic suspension vehicles provided herein may include at least one salt. According to one embodiment, the at least one salt is sodium chloride or other suitable salt for ophthalmic application. The at least one salt may be present in an amount of from about 0.50 percent weight to about 0.75 percent weight. According to another embodiment, the at least one salt may be present in an amount of from about 0.55 percent weight to about 0.70 percent weight. According to another embodiment, the at least one salt may be present in an amount of about 0.55 percent weight. According to another embodiment, the at least one salt may be present in an amount of about 0.67 percent weight.

According to one embodiment, the ophthalmic suspension vehicles provided herein may include at least one glycosylaminoglycan. A suitable glycosylaminoglycan includes hyaluronic acid (HA), the corresponding sodium salt, sodium hyaluronate, or a combination thereof. According to one embodiment, the hyaluronic acid or sodium hyaluronate may be present in the ophthalmic suspension vehicle in an amount of from about 0.06 percent about to about 0.5 percent weight. According to one embodiment, the hyaluronic acid or sodium hyaluronate may be present in the ophthalmic suspension vehicle in an amount of from about 0.07 percent about to about 0.4 percent weight. According to one embodiment, the hyaluronic acid or sodium hyaluronate may be present in the ophthalmic suspension vehicle in an amount of from about 0.08 percent about to about 0.3 percent weight. According to one embodiment, the hyaluronic acid or sodium hyaluronate may be present in the ophthalmic suspension vehicle in an amount of from about 0.09 percent about to about 0.2 percent weight. According to one embodiment, the hyaluronic acid or sodium hyaluronate may be present in the ophthalmic suspension vehicle in an amount of about 0.1 percent weight.

According to one embodiment, the ophthalmic suspension vehicles provided herein optionally include ethylenediaminetetraacetic acid (EDTA). According to one embodiment, the EDTA may be present in the ophthalmic suspension vehicle in an amount of from about 0.007 percent weight to about 0.02 percent weight. According to one embodiment, the EDTA may be present in the ophthalmic suspension vehicle in an amount of from about 0.008 percent weight to about 0.015 percent weight. According to one embodiment, the EDTA may be present in the ophthalmic suspension vehicle in an amount of about 0.01 percent weight.

According to one embodiment, in addition to one or more pharmaceutical ingredients, the ophthalmic suspension vehicles provided herein optionally include at least one anti-inflammatory compound such as deactivated brewer's yeast or adenosine diphosphate ribose. When present, the at least one anti-inflammatory compound does not impact ophthalmic suspension vehicle stability or on-eye performance. According to one embodiment, the anti-inflammatory compound may be present in the ophthalmic suspension vehicle in an amount of from about 0.02 percent weight to about 1.0 percent weight.

According to one embodiment, the ophthalmic suspension vehicles provided herein may have an osmolality that can be adjusted by the concentration of salts such as NaCl. According to one embodiment, the ophthalmic suspension vehicles provided herein have osmolality of at least about 245 mOsmol/kg. According to one embodiment, the ophthalmic suspension vehicle provided herein has an osmolality of at least about 260 mOsmol/kg. According to one embodiment, the ophthalmic suspension vehicles provided herein have an osmolality of from about 245 mOsmol/kg to about 315 mOsmol/kg. According to one embodiment, the ophthalmic suspension vehicles provided herein have an osmolality of from about 245 mOsmol/kg to about 310 mOsmol/kg. According to one embodiment, the ophthalmic suspension vehicles provided herein have an osmolality of from about 255 mOsmol/kg to about 305 mOsmol/kg. According to one embodiment, the ophthalmic suspension vehicles provided herein have an osmolality of from about 270 mOsmol/kg to about 300 mOsmol/kg. According to one embodiment, the ophthalmic suspension vehicles provided herein have an osmolality of from about 275 mOsmol/kg to about 295 mOsmol/kg. According to one embodiment, the ophthalmic suspension vehicles provided herein have an osmolality of from about 280 mOsmol/kg to about 290 mOsmol/kg. According to one embodiment, the ophthalmic suspension vehicles provided herein have an osmolality of from about 282 mOsmol/kg to about 289 mOsmol/kg. According to one embodiment, the ophthalmic suspension vehicles provided herein have an osmolality of from about 285 mOsmol/kg to about 287 mOsmol/kg. According to one embodiment, the ophthalmic suspension vehicles provided herein have osmolality of about 286 mOsmol/kg.

According to one embodiment, the ophthalmic suspension vehicles provided herein have a pH of between about 6.8 and 7.8. According to one embodiment, the ophthalmic suspension vehicles provided herein exhibit a pH of between about 6.9 and 7.7. According to one embodiment, the ophthalmic suspension vehicles provided herein exhibit a pH of between about 7.0 and 7.6. According to one embodiment, the ophthalmic suspension vehicles provided herein exhibit a pH of between about 7.0 and 7.4. According to one embodiment, the ophthalmic suspension vehicles provided herein exhibit a pH of between about 7.1 and 7.5. According to one embodiment, the ophthalmic suspension vehicles provided herein exhibit a pH of between about 7.2 and 7.4. According to one embodiment, the ophthalmic suspension vehicles provided herein exhibit a pH of about 7.2. According to one embodiment, the ophthalmic suspension vehicles provided herein exhibit a pH of about 7.3. The pH may be adjusted by addition of pH adjusters such as HCl or citric acid or a base such as NaOH.

The viscosity of the ophthalmic suspension vehicles described herein may vary but will exhibit a viscosity allows appropriate drop size for application to the eye. According to one embodiment, the viscosity of the ophthalmic suspension vehicles provided herein exhibit a viscosity of from about 5 centipoise at 25° C. to about 8 centipoise at 25° C. The viscosity of the ophthalmic suspension vehicles described herein may be measured using techniques well-known to those skilled in the art. Non-limiting examples of methods to measure viscosity include falling ball viscometers, viscosity cups, consistometers (measuring flow on an incline), capillary glass viscometers, or rotational viscometers. A variety of instruments are commercially available (Cole-Palmer Instrument Co., Vernon Hills, IL, USA).

The ophthalmic suspension vehicles provided herein may be preservative-free. In some embodiments, preservative-free ophthalmic suspension vehicle is delivered in single use packages because of the risk of bacterial contamination associated with conventional multi-use applications. In another embodiment, the ophthalmic suspension vehicles are delivered in a sterile multidose bottle. Examples include the Aptar Pharma (Crystal Lake, IL, USA) multidose squeeze dispenser which operates mechanically and utilizes a filter membrane (see PCT Publication Nos. WO 2017/074420 and WO 2017/132190 (Aptargroup, Inc.); Nemera La Verpillier (France) multidose squeeze bottle (see PCT Publication WO2013/140069)), each incorporated by reference with regard to such containers.

According to an alternative embodiment, the ophthalmic suspension vehicles provided herein may optionally include at least one preservative. The amount of preservative does not negatively impact ophthalmic suspension vehicle stability, on-eye performance, or create an adverse effect to the user. According to an alternative embodiment, the ophthalmic suspension vehicles provided herein may include at least one borate buffer.

The pharmaceutical ingredients suitable for delivery to the eye via the ophthalmic suspension vehicles provided herein include those soluble in either the aqueous phase or oil phase of the ophthalmic suspension vehicle. Classes of suitable pharmaceutical ingredients include antibiotics, antiviral agents, anti-inflammatory agents and antiglaucoma agents such as illustrated in part in published European Patent Application No. 0 092 453 published Oct. 26, 1983, sections 5.3.1 and 5.3.2, or PCT Pub. No. WO 2015/05531 published Apr. 23, 2015, page 5, lines 5-22, incorporated herein by reference. Other suitable pharmaceutical ingredients include, but are not limited to, adenosine diphosphate ribose, antazoline, apraclonidine, apraclonidine, atropine, azelastine, bepotastine, etamethasone, betaxolol, betaxolol, bimatoprost, brimonidine, brinzolamide, bromfenac, bromfenac, cardiolipin peroxidation inhibitors, carteolol, cetrimide, chloramphenicol, ciprofloxacin, cyclosporine, dexamethasone, diclofenac, dorzolamide, emedastine, epinastine, epinastine, flurbiprofen, framycetin sulphate, gentamycin, gramicidin, *hamamelis* water, homatropine, hyaluronic acid, ketotifen fumarate, lacritin/lacritin protein fragment, latanoprost, levobunolol, levofloxacin, lodoxamide loteprednol, lymphocyte function associated antigen 1 (LFA-1) antagonist, modified 19-kDa TNF receptor, moxifloxacin, naphazoline, naphazoline, nedocromil maleate, nicotinic acetylcholine receptor (nAChR) agonist, ofloxacin, olopatadine, pegaptanib, perfluorohexyloctane, pheniramine, pilocarpine, pranoprofen, prednisolone, ranibizumab, reactive aldehyde species inhibitor, recombinant lubricin, rimexolone, sodium, tetracaine, tetrahydrozoline, thiomersal, timolol, tobramycin, trafluprost, travoprost, ketorolac trometamol, trometamol, xylometazoline or any combination thereof. According to one embodiment, the at least one pharmaceutical ingredients suitable for delivery to the eye via the ophthalmic suspension vehicle is a cannabidiol, tetrahydrocannabinol, or a combination thereof. Other pharmaceutical ingredients and combinations thereof, while not explicitly named, should be considered as available for delivery with the ophthalmic suspension vehicle of the present disclosure.

According to one embodiment, the at least one pharmaceutical ingredient is a neutral lipid or oil such as one or more triglycerides, partially hydroylyzed esters, cholesterol esters, and high molecular weight isoprenoids. According to one embodiment, the at least one pharmaceutical ingredient is a stabilizer, surfactant, mucomimetic (e.g., HP Guar), preservative, pH adjuster, salt, buffer, glycerol, sugar, emollient, or demulcent. According to one embodiment, the at least one pharmaceutical ingredient is a polymer of ethylene oxide, propylene oxide, or butylene oxide. According to one embodiment, the at least one pharmaceutical ingredient is a carboxymethylcellulose (CMC), hydroxypropyl methylcellulose (HPMC), polyacrylic acid (PAA), polyethylene glyco, (PEG) propylene glycol (PG), or polyvinyl alcohol (PVA).

Methods of preparing ophthalmic suspension vehicles are provided. According to one embodiment, the method of preparation of the ophthalmic suspension vehicle includes the step of separately preparing a mixture of the oils (e.g., heavy weight mineral oil and light weight mineral oil) and adding the wax ester component, such as beeswax, and heating the mixture to a temperature above the melting point of the wax ester (e.g., from about 63° C. to about 71° C.). In a separate water/aqueous phase, the salts, phosphates, surfactants and any other water-soluble ingredient may be prepared and heated to approximately 85° C. The oil phase may then be slowly added to the water/aqueous phase, mixed, and homogenized to form the ophthalmic suspension vehicle. The resulting ophthalmic suspension vehicle is autoclaved. Throughout the process, the ophthalmic suspension vehicle continues to be mixed.

According to one embodiment, the method of preparation of the ophthalmic suspension vehicle includes the step of separately preparing the oil phase (e.g., heavy weight mineral oil and light weight mineral oil) heating to a temperature of from about 63° C. to about 71° C. The step of preparing the oil phase may optionally include the step of adding or introducing at least one wax ester to the oil phase followed by heating the mixture to a temperature above the melting point of the wax ester (e.g., from about 63° C. to about 71° C.).

According to one embodiment, the method of preparation of the ophthalmic suspension vehicle includes the step of separately preparing the aqueous phase. The aqueous phase may be prepared by mixing the at least one wax ester, at least one salt, at least one phosphate, at least one surfactant and any other water-soluble ingredient followed by heating the mixture to a temperature above the melting point of the wax ester (e.g., from about 63° C. to about 71° C.).

According to one embodiment, the oil phase as provided herein may then slowly added to the aqueous phase, mixed, and homogenized to form the ophthalmic suspension vehicle. The resulting ophthalmic suspension vehicle may then be autoclaved. Thus, according to such an embodiment, the individual oil phase and aqueous phase are not separately autoclaved prior to being combined. According to one embodiment, the resulting ophthalmic suspension vehicle is not autoclaved and sterilized according to an alternative method such as, for example, e-beam or gamma irradiation, or filtration.

According to an alternative embodiment, a method of preparing an ophthalmic suspension vehicle is provided. This alternative method includes the step of preparing a wax dispersion by mixing or dissolving at least one wax ester (such as a natural beeswax) with a surfactant and purified or deionized water. According to one embodiment, the at least one wax ester may be mixed or dissolved in such a way that the natural wax esters can be delivered in a controlled manner leading to increased dwell time on the eye. According to one embodiment, the step of preparing a wax dispersion includes dissolving one or more salts and one or more phosphates such as a monosodium phosphate and disodium phosphate in the purified or deionized water. According to one embodiment, the step of preparing a wax dispersion includes heating the one or more salts, phosphates, surfactants and wax esters and stirring the resulting dispersion. According to one embodiment, the dispersion is heated to about 70° C. to about 90° C. According to a particular embodiment, wax ester particle dispersions may be prepared by homogenization of melted beeswax (~1.0%) in purified or distilled water containing salts, phosphates with added Octoxynol-40 (~0.2% 1,2-Dimyristoyl-sn-glycero-3-phosphorylglycerol sodium salt (DMPG)) at about 75° C. The high cloud point of Octoxynol-40 (>100° C.) allows emulsifying efficiency at higher temperatures by a decrease in its water solubility (effective lowering of the HLB value).

The alternative method includes the step of preparing an oil-in-water emulsion. According to one embodiment, the step of preparing an oil-in-water emulsion includes mixing differing weight or viscosity of mineral oils as described herein and heating the mixture of mineral oils to a temperature of from about 65° C. to about 75° C. According to one embodiment, the step of preparing an oil-in-water emulsion includes dropwise introducing the mixture of heated mineral oils to purified or deionized water and homogenizing the water and mineral oil mixture to form an oil-in-water emulsion. The pH of the oil-in-water emulsion may be adjusted to a range of from about 6.8 to about 7.8.

The alternative method includes the step of separately autoclaving the wax dispersion and the oil-in-water emulsion. The integrity of the emulsion is maintained during autoclaving.

While not being bound to a particular theory, the mechanism involved in the irreversible aggregation of the wax (wax breakout) under autoclave conditions is believed to involve the presence of relatively high (approximately isotonic) salt concentrations. This high ionic loading is believed to significantly decrease the zeta-potential of the wax ester particles, which removes an important stabilization mechanism when these dispersions are subjected to autoclave conditions.

The alternative method includes the step of aseptically blending the autoclaved beeswax dispersion and the oil-in-water emulsion so as to prepare the ophthalmic suspension vehicles as provided herein. According to one embodiment, the wax ester particles may be stabilized by the surfactant in the oil phase preventing flocculation and droplet aggregations during cooling.

To maintain a shelf stable vehicle, separate preparation and autoclaving of the wax ester particle dispersion and emulsion components may be performed, followed by an aseptic blending step to ensure product sterility according to the alternative method. The aseptic blending step of the autoclaved beeswax dispersion and the oil-in-water emulsion ensures that the desired final concentrations of mineral oil, beeswax, and other components are present in the ophthalmic suspension vehicle. The oil-in-water emulsion is formulated with increased component levels, while the beeswax ester particles are emulsified in water with an added surfactant. The concentrations of the various components in the two fractions (before autoclaving) can be tailored to permit a relatively wide variation of final emulsified vehicle compositions.

Example 1

Preparation of Ophthalmic Suspension Vehicle Including Pharmaceutical Ingredient An exemplary ophthalmic suspension vehicle was prepared including the components set forth in Table 1, below.

TABLE 1

| Component | Weight % |
|---|---|
| Water | 89.95-94.00 |
| ADP-Ribose | 0.05-1.00 |
| NaCl | 0.10-0.90 |
| $NaH_2PO_4$ | 0.01-0.05 |
| $Na_2HPO_4$ | 0.10-0.50 |
| Tween-80 | 0.10-0.70 |
| DMPG | 0.35-0.55 |
| Wax ester | 0.80-1.20 |
| Sodium Hyaluronate | 0.06-0.50 |
| Drakeol ®-35 | 2.7-6.5 |
| Drakeol ®-15 | 0.50-1.50 |

To prepare a 500 gram batch of the ophthalmic suspension vehicle, NaCl, dimyristoylphosphatidylglycerol (DPMG), $NaH_2PO_4$ and $Na_2HPO_4$ were dissolved in purified water in a beaker. Tween 80, DPMG, ADP-Ribose and sodium hyaluronate were added to the aqueous solution and heated with continuous stirring to 85° C. (+/−2° C.). In a separate glass beaker, Drakeol® 15, Drakeol® 35 and wax ester were mixed and heated to 71° C. (+/−2° C.) with continuous stirring for 10 minutes (+/−20 seconds). The aqueous phase was homogenized for 30 seconds (+/−5 seconds). The oil phase was pre-heated to 71° C. (+/−2° C.) and added dropwise to the aqueous phase at 85° C. (+/−2° C.), while the homogenizer was running. After the addition of the oil was complete, the homogenizer was run. The target homogenization speed was around 10,000 RPM (+/−400 RPM) and the target homogenization time was about 4 min (+/−20 seconds). The homogenization procedure was terminated and stirring continued until the vehicle reached room temperature (approximately 4 hours). While stirring, the pH and osmolality were checked and adjusted (target pH: 7.2-7.4: osmolality of 240 mOsmol/kg-290 mOsmol/kg). While stirring, the vehicle mixture was dispensed using a syringe to an autoclavable bottle and charged with a magnetic stir bar. The bottle and autoclave were closed for 35 minutes (+/−1 minute) and heated to/at 121° C. and 15 psi while stirring. The ophthalmic suspension vehicle was allowed to cool to room temperature while stirring (approximately 6 hours).

Example 2

Ophthalmic Pharmaceutical Ingredient in a Suspension Vehicle—On-Eye Performance

A study was conducted to evaluate the on-eye performance of the ophthalmic suspension vehicle with a known anti-inflammatory agent ADP-Ribose as set forth in Table 1. The study yielded positive results both in terms of the suspension vehicle properties and on-eye performance. Particularly, studies were conducted on patients who exhibited diminished tear film with low levels of lipid layer thickness (LLT) based on previous and day-of screenings. The thickness of the lipid layer of the tear film at baseline using interferometry was measured. The baseline lipid layer thickness for these patients ranged from 25 nm to 70 nm with an average of 45 nm. A lipid layer thickness of less than 70 nm was considered deficient.

After the baseline measurements were taken, a single test drop of the ophthalmic suspension vehicle in Table 1 (of Example 1) and a single control drop were self-instilled in contralateral eyes. The control drop selected was the solution commercially available as Systane® Ultra PF (commercially available, a non-lipid containing drop that is free of preservatives).

With the main objective being an evaluation of duration on the eye by the increase of lipid layer thickness, the first challenge was to develop a rigorous inclusion and exclusion criteria for patient recruitment to select subjects that had a chronically desiccated tear film due to Evaporative Dry Eye (e.g., Meibomian Gland Dysfunction or MGD), rather than partial blinking or a side effect of another medication or procedure. Primarily, this study sought subjects with a baseline lipid layer thickness of less than 55 nm in at least one eye, and less than 50% partial blinking rate, both measured using the LipiView (Johnson and Johnson).

Once inclusion criteria were established, a formal protocol for the clinician and staff to follow had to be created. In this document, each step of the patient evaluation process was laid out in a checkbox format; from initial patient evaluation and day-of confirmation of inclusion to the actual evaluation and measurement processes.
1. Inclusion determination
2. Exclusion confirmation
3. Ocular health exam (Evaluation specifics were at the physician's discretion)
4. Baseline LLT reading
5. SPEED Pre-assessment
    (Standard Patient Evaluation of Eye Dryness), see Korb et al. Lid wiper epitheliopathy and dry eye symptoms, *Eye Contact Lens.* 2005 January; 31(1):2-8: and Korb et al. The effect of two novel lubricant eye drops on tear film lipid layer thickness in subjects with dry eye symptoms. *Optom Vis Sci.* 2005 July; 82(7):594-601, each incorporated by reference with regard to such survey testing.
6. Test and Control Drop Instillation
7. Measurement at 5, 30, 60, 120, 180, and 240-minute time intervals
8. SPEED Post-Assessment The drops were masked to the patients, but not masked for the physician and staff. All study results were recorded on a data record form with patient identity masked.

Over the course of two weeks, 12 patients completed the study. The results, as illustrated in Tables 2 and 3, show the raw average lipid layer thickness readings for the 12 patients measured. The ophthalmic suspension vehicle of Table 1 showed a significant increase in lipid layer thickness at the 5 and 30-minute time points. At all-time points, there was significant separation between the ophthalmic suspension vehicle and the control drop. The ophthalmic suspension vehicle maintained a 72.5 (+/−3.8) nm average lipid layer thickness at the 4-hour mark compared with the control at 61.8 (+/−2.2) nm.

TABLE 2

Ophthalmic Suspension Vehicle with Pharmaceutical Ingredient

| Time Interval | Lipid Layer Thickness (nm) |
|---|---|
| Baseline | 49.5 |
| 5 Minutes | 79.2 |
| 30 Minutes | 77.6 |
| 60 Minutes | 70.2 |
| 120 Minutes | 74.0 |
| 180 Minutes | 70.4 |
| 240 Minutes | 72.5 |

TABLE 3

Systane ® Ultra

| Time Interval | Lipid Layer Thickness (nm) |
|---|---|
| Baseline | 57.6 |
| 5 Minutes | 66.8 |
| 30 Minutes | 66.2 |
| 60 Minutes | 61.3 |
| 120 Minutes | 61.1 |
| 180 Minutes | 63.5 |
| 240 Minutes | 61.2 |

Based on the raw data from contralateral eyes, differences emerged in the average baseline lipid layer thickness in the test and control eyes. Thus, in addition to using lipid layer thickness at each time point as a key metric, the average increase from baseline in lipid layer thickness across patients with both the test and control drops was evaluated. Table 4 provides the lipid layer thickness increase obtained from the ophthalmic suspension vehicle as set forth in Table 1. Table 5 provides the lipid layer thickness increase obtained from the Systane® Ultra PF solution.

Clear separation of the test and control drops at every time point are illustrated, with the ophthalmic suspension vehicle showing a nearly 50% increase in lipid layer thickness at the 4-hour mark. Thus, reduction in lipid layer thickness is delayed to well beyond the 4-hour mark before returning to baseline. If the degradation rate remains linear, a significant lipid layer thickness increase is likely to extend well beyond 8 hours using only a single drop of the ophthalmic suspension vehicle.

TABLE 4

Ophthalmic Suspension Vehicle with Pharmaceutical Ingredient

| Time Interval | Increase In Lipid Layer Thickness (nm) | Percentage Increase in Lipid Layer Thickness |
|---|---|---|
| 5 Minutes | 29.7 | 59.9% |
| 30 Minutes | 28.1 | 56.7% |
| 60 Minutes | 20.7 | 41.8% |
| 120 Minutes | 24.5 | 49.5% |
| 180 Minutes | 20.9 | 42.3% |
| 240 Minutes | 23.0 | 46.5% |

TABLE 5

Systane ® Ultra

| Time Interval | Increase In Lipid Layer Thickness (nm) | Percentage Increase in Lipid Layer Thickness |
|---|---|---|
| 5 Minutes | 9.2 | 15.9% |
| 30 Minutes | 8.6 | 14.9% |
| 60 Minutes | 3.7 | 6.4% |
| 120 Minutes | 3.5 | 6.1% |
| 180 Minutes | 5.9 | 10.4% |
| 240 Minutes | 4.2 | 7.4% |

Two subjective questions were asked to patients immediately upon drop instillation for each eye. The first question asked patients to score their initial comfort from 0-100. The second question was to report the duration of any visual blurring they noticed. For the ophthalmic suspension vehicle, the average patient noted an 85 out of 100 comfort score and 5.6 seconds of minimal visual blurring. For the control drop the average results were 92 out of 100 and 2.9 seconds. While there is a difference on both of these subjective metrics between test and control, blurring was less than 3 seconds longer for the ophthalmic suspension vehicle, while initial comfort score varied by 7 out of 100.

Most patients reported no blurring for the ophthalmic suspension vehicle, with the longest blur duration was 30 seconds (one in test eye and one in control eye). The patient comfort scores were similar and ranged from 45 to 100 in the test eye and 50 to 100 in the control eye. Based on thousands of hours of in-house testing, the comfort and blur are similar to the control solution.

A self-administered SPEED dry eye symptom questionnaire was incorporated into this study. A score of 8 or greater indicated the presence of dry eye. Patients responded with an average SPEED score of 13.58 at the beginning of the test, prior to drop instillation.

After 4 hours elapsed after drop instillation, patients were re-tested using SPEED. The average result for the post assessment was a score of 10.5, with no patients reporting an increased score and five patients reporting a score of less than 8. The assessment did not distinguish symptoms between eyes. Since the experiment was conducted in contralateral eyes, the delineating effect of the ophthalmic suspension vehicle versus the control drops was difficult. The SPEED assessment was meant to gauge symptoms over a span of weeks or months, so an immediate result may not be an accurate reflection of the patient's symptoms. Finally, the time of day was a variable not controlled for in this study and may have had an effect on patient-reported symptoms.

In summary, this study demonstrated a significant increase of on-eye duration of the suspension vehicle which was demonstrated relative to control over a four-hour interval in an arms-length, physician-administered study. Particularly, the ophthalmic demonstrated a nearly 50% increase in tear film thickness at the 4-hour mark in a controlled on-eye patient evaluation thereby demonstrating the ophthalmic suspension can be used as a vehicle for drug delivery for long term on eye activity.

While not being bound to a particularly theory, as wax ester particles are dissolving, the oil bound with the wax ester particles is believed to be released into the tear film and migrates to the surface, continuously replenishing the patient's diminished evaporative lipid barrier. Differently-sized particles dissolve at different rates. In effect, the wide distribution of oil-bound wax ester particles creates a controlled-release mechanism that delivers lipids into the tear film with every blink as the wax ester particle is dissolved. The wax ester is believed to act as a mechanism to slow the lipid layer from draining through the puncta during the course of regular tear turnover.

Example 3

Particle Size

In order to provide the desired pharmaceutical ingredient delivery characteristics, the oil and wax ester portion of the ophthalmic vehicle is retained in the ocular environment for an extended period of time. Wax ester particle size is preferably maintained to provide for long lasting lipid layer increases on eye over time.

Particle size was determined utilizing a Microtrac Sync 3R Flow device. Particle size analysis was carried out using samples of about 6.0 mL of the ophthalmic vehicle of Example 1. The samples were stored in plastic bottles until testing. Prior to testing, each bottle was shaken 10 times. The entire cap was then removed and approximately two drops of sample were transferred to the Microtrac Sync 3R Flow device using a plastic pipette. The sample was loaded to the particle size analyzer. Approximately two drops (0.060 g) of sample were injected into a 200 mL deionized water circulating chamber and testing was initiated.

Results from mineral oil alone indicated that the loss of added mineral oil does not extend beyond 30 minutes as observed in the competitive product, Systane® Balance. The results are summarized in Table 6.

The processing parameter labeled "Homogenizer" in Table 6 refers to processing by only the homogenizer in the range of from about 10 k to about 18 k rpm for about 4 to about 8 minutes. The other processing parameters refer to the pressure of the micofluidizer system utilized to evaluate homogeneity. This additional processing was added after initial homogenization and resulted in a reduction in particle size but decreased the clinical performance (average increase in over baseline). More specifically, based on particle size analysis conducted on several test formulas, the homogenizer-only process yielded mean particle sizes in the 2 to 20 micron range while samples further processed with a microfluidizer yields mean particle sizes of ≤1 micron. Actual measurements of the formulations determined the significant range for particle size and distribution. Specifically, formulations with mean particle sizes of about 1 micron do not remain in the eye, while the best-performing formulas had a mean particle size in the 5 to 20 micron range under the conditions of the measurement.

TABLE 6

| Processing Parameter (kpsi) | Average of Mean Particle Size (nm) | Average Increase (nm) Over Baseline Relative to Control: 5 Minutes | Average Increase (nm) Over Baseline Relative to Control: 30 Minutes | Average Increase (nm) Over Baseline Relative to Control: 60 Minutes | Average Increase (nm) Over Baseline Relative to Control: 120 Minutes | N |
|---|---|---|---|---|---|---|
| Homogenizer | 13.6 | 19.2 | 22.1 | 20.7 | 17.4 | 32 |
| 2.5 | 4.7 | 7.9 | 14.4 | 12.5 | 13.1 | 8 |
| 5 | 8.9 | 13.8 | 16.0 | 21.0 | 8.3 | 6 |
| 10 | 2.3 | 2.1 | 21.6 | 14.9 | 6.7 | 7 |
| 15 | 1.7 | −1.3 | 3.5 | 22.3 | 6.8 | 6 |
| 20 | 0.9 | 0.3 | 4.4 | 4.8 | 6.8 | 10 |

Example 4

Zeta Potential and Ionic Mobility Analysis

Zeta potential testing was conducted to evaluate particle performance and stability of various ophthalmic vehicles versus an ophthalmic drop commercially available as Systane© Balance. Zeta potential indicates the degree of electrostatic repulsion between similarly charged particles in a dispersion. In general, a high negative zeta potential correlates to stability (e.g., a dispersion will resist aggregation). In the ophthalmic context, the applicant has demonstrated a higher negative potential directly translates to longer dwell time of an ophthalmic vehicle on the eye.

Ionic mobility testing was conducted on the same ophthalmic vehicles and Systane® Balance eye drop to evaluate the particle velocity generated by an electric field.

The content of the ophthalmic vehicles tested (samples A-F) are show in Table 7. Sample A was homogenized at a speed of 10,000 RPM for two minutes with beeswax added into the aqueous phase. Sample B was homogenized at a speed of 20,000 RPM for eight minutes with beeswax added into the aqueous phase. Samples C and D were homogenized at a speed of 18,000 RPM for eight minutes with beeswax added into the aqueous phase. Samples E and F were homogenized at a speed of 18,000 RPM for eight minutes with beeswax added into the oil phase with the oil and water phases separated and tested. The Systane® Balance eye drop included propylene glycol (0.6%) lubricant as the primary active ingredient along with various inactive ingredients including boric acid, dimyristoylphosphatidylglycerol, edetate disodium, hydroxypropyl guar, mineral oil, polyoxyl 40 stearate, POLYQUAD® (polyquaternium-1) 0.001% preservative, sorbitan tristearate, sorbitol and purified water, as well as hydrochloric acid and/or sodium hydroxide to adjust pH.

The results of the zeta potential and ionic mobility testing are provided in Table 8.

TABLE 7

| Component | Weight (% w/w) | | | | | |
|---|---|---|---|---|---|---|
| Sample | A | B | C | D | E | F |
| Water | 91.65 | 91.37 | 91.67 | 91.67 | 91.67 | 91.67 |
| NaCl | 0.67 | 0.55 | 0.55 | 0.55 | 0.55 | 0.55 |
| NaH2PO4 | 0.03 | 0.03 | 0.03 | 0.03 | 0.03 | 0.03 |
| Na2HPO4 | 0.25 | 0.25 | 0.25 | 0.25 | 0.25 | 0.25 |
| Tween-80 | 0.4 | 0.6 | 0.4 | 0.4 | 0.4 | 0.4 |
| DMPG | 0.4 | 0.6 | 0.5 | 0.5 | 0.5 | 0.5 |
| Beeswax | 1 | 1 | 1 | 1 | 1 | 1 |
| HA | 0.1 | 0.1 | 0.1 | 0.1 | 0.1 | 0.1 |
| Drakeol ®-35 | 4.5 | 4.5 | 4.5 | 4.5 | 4.5 | 4.5 |
| Drakeol ®-15 | 1 | 1 | 1 | 1 | 1 | 1 |

TABLE 8

| Sample | $\zeta$ Potential (mV) | $\mu$ Ionic Mobility (μm/s)/(V/cm) |
|---|---|---|
| A | −76 | −5.9 |
| B | −94 | −7.4 |
| C | −80 | −6.3 |
| D | −93 | −7.2 |
| E | −81 | −6.3 |
| F | −90 | −7.1 |
| Systane ® Balance | −6 | −0.5 |

Ophthalmic vehicles A-F all demonstrated a zeta potential of from about −75 to about −95 and an ionic mobility of from about −6 to about −7.5. These results demonstrate that ophthalmic vehicles as provided herein provide sizable stabilization of large particles as well as sustained thickening of tear film, unlike that of the Systane® Balance eye drop which demonstrated markedly different zeta potential and ionic mobility.

Example 5

Ophthalmic Vehicles Compared to Commercial Artificial Tears

A study was conducted to evaluate the on-eye performance of the ophthalmic vehicle as set forth in Table 1 versus different commercially available artificial tear products (HyloCare®, Tears Again, Cationorm®, Hylovision®, Thealoz®, EvoTears®, TheraTears®, Systane® Complete, Systane® Balance, Soothe®XP, Retaine® MGD and Refresh Optive® Advanced).

Lipid layer thickness measurements of the commercial products were taken out to 60 minutes. The ophthalmic vehicle was measured to 120 minutes and beyond. The testing was open-label and utilized Systane Ultra PF® as the control. A total of 93 observations (n=93) among the 12 commercially available products were made. The results show that no product was able to increase lipid layer thickness 13 nm over the control at the 5-minute time interval, and the best performing commercial product showed an increase in 10 nm over control at the 60-minute time interval.

On average, an increase in 21 nm over the control at the 5-minute time interval with the lipid layer thickness continuing to increase to 24.7 nm at the 60-minute time point (n=78). The aggregated data is summarized in Tables 9 and 10.

TABLE 9

| Ophthalmic Vehicle (n = 78) | |
|---|---|
| Time Interval | Increase In Lipid Layer Thickness (nm) From Baseline |
| 5 Minutes | 20 |
| 30 Minutes | 24 |
| 60 Minutes | 23 |

TABLE 10

| Commercial Product (n = 93) | |
|---|---|
| Time Interval | Increase In Lipid Layer Thickness (nm) From Baseline |
| 5 Minutes | 5 |
| 30 Minutes | 3 |
| 60 Minutes | 2 |

In aggregate, the ophthalmic vehicles showed a five times (5×) improvement in immediate lipid layer thickness increase over 78 cumulative observations compared with the 93 cumulative observations of the 12 commercially available products. This gap in lipid layer thickness increase is eleven times (11×) at the 60-minute mark with the ophthalmic vehicle showing a 23 nm increase over baseline relative to control versus the commercial products only showing a two nm increase over baseline relative to control.

It should be understood that the above description is only representative of illustrative embodiments and examples. For the convenience of the reader, the above description has focused on a limited number of representative examples of all possible embodiments, examples that teach the principles of the disclosure. The description has not attempted to exhaustively enumerate all possible variations or even combinations of those variations described. That alternate embodiments may not have been presented for a specific portion of the disclosure, or that further undescribed alternate embodiments may be available for a portion, is not to be considered a disclaimer of those alternate embodiments. One of ordinary skill will appreciate that many of those undescribed embodiments, involve differences in technology and materials rather than differences in the application of the principles of the disclosure. Accordingly, the disclosure is not intended to be limited to less than the scope set forth in the following claims and equivalents.

It is to be understood that, while the disclosure has been described in conjunction with the detailed description, thereof, the foregoing description is intended to illustrate and not limit the scope. Other aspects, advantages, and modifications are within the scope of the claims set forth below.

Generalized Statements of the Disclosure

The following numbered statements provide a general description of the disclosure and are not intended to limit the appended claims.

Statement 1. An ophthalmic suspension vehicle is provided that includes a wax dispersion including at least one wax ester, an anionic polar surfactant and water; and an oil-in-water emulsion that includes at least one oil and water. The wax ester exhibits a mean particle size of at least about 5.0 microns using a Microtrac particle analyzer procedure to determine particle size.

Statement 2. The present disclosure provides an ophthalmic emulsified vehicle of Statement 1.

Statement 3. The present disclosure provides an ophthalmic suspension vehicle of any of Statements 1-2, wherein the ophthalmic suspension vehicle has an osmolality of from about 245 mOsmol/kg to about 315 mOsmol/kg.

Statement 4. The present disclosure provides an ophthalmic suspension vehicle of any of Statements 1-3, wherein the ophthalmic suspension vehicle is formulated as a free flowing emulsified vehicle at about 30° C.

Statement 5. The present disclosure provides an ophthalmic suspension vehicle of any of Statements 1-4, wherein the wax ester is present in a concentration of about 0.8 weight percent to about 1.2 weight percent.

Statement 6. The present disclosure provides an ophthalmic suspension vehicle of any of Statements 1-5, wherein the wax ester is a natural beeswax.

Statement 7. The present disclosure provides an ophthalmic suspension vehicle of any of Statements 1-6, wherein the ophthalmic suspension vehicle exhibits a negative zeta potential of from about −60 mV to about −110 mV.

Statement 8. The present disclosure provides an ophthalmic suspension vehicle of any of Statements 1-7, wherein the ophthalmic suspension vehicle exhibits an ionic mobility of from about −5.9 (µms)/(V/cm) to about −7.4 (µms)/(V/cm).

Statement 9. The present disclosure provides an ophthalmic suspension vehicle of any of Statements 1-8, wherein the oil is a mixture of a lightweight mineral oil and a heavy weight mineral oil.

Statement 10. The present disclosure provides an ophthalmic suspension vehicle of any of Statements 1-9, wherein the lightweight mineral oil exhibits a kinetic viscosity of from about 3.0 $mm^2s^{-1}$ to about 34.4 $mm^2s^{-1}$ at 40° C. and the heavy weight mineral oil exhibits a viscosity of kinetic viscosity of from about 34.5 $mm^2s^{-1}$ to about 150 $mm^2s^{-1}$ at 40° C.

Statement 11. The present disclosure provides an ophthalmic suspension vehicle of any of Statements 1-10, further including an anionic polar surfactant comprising a mixture of a polysorbate non-ionic surfactant at a concentration of about 0.35 to about 0.45 weight percent and an anionic polar dimyristoylphosphatidylglycerol at a concentration of about 0.35 to about 0.55 weight percent.

Statement 12. The present disclosure provides an ophthalmic suspension vehicle of any of Statements 1-11, packaged in a sterile multi-use or sterile single use container.

Statement 13. The present disclosure provides an ophthalmic suspension vehicle of any of Statements 1-12, packaged in a multi-dose non-preserved (MDNP) container or a container including at least one preservative.

Statement 14. The present disclosure provides an ophthalmic suspension vehicle of any of Statements 1-13, wherein ophthalmic suspension vehicle increases lipid layer thickness by at least 20 nanometers at five minutes after administration.

Statement 15. The present disclosure provides an ophthalmic suspension vehicle of any of Statements 1-14, wherein the ophthalmic suspension vehicle increases lipid layer thickness by at least 20 nanometers at four hours after administration.

Statement 16. A method of increasing lipid layer thickness is provided and includes the step of administering an ophthalmic suspension vehicle of any of Statements 1-15 to an eye of a patient in need of treatment.

Statement 17. The present disclosure provides a method of increasing lipid layer thickness of Statement 16, wherein the lipid layer thickness is increased by at least 20 nm within five minutes of administration.

Statement 18. The present disclosure provides a method of increasing lipid layer thickness of any of Statements 16-17, wherein the lipid layer thickness is increased by at least 20 nm at four hour after administration.

Statement 19. The present disclosure provides a method of lubricating an eye including administering to the eye an ophthalmic suspension vehicle of any of Statements 1-15 to an eye of a patient in need of treatment.

Statement 20. The present disclosure provides a method of for alleviating the symptoms of dry eye including administering to the eye an ophthalmic suspension vehicle of any of Statements 1-15 to an eye of a patient in need of treatment.

Statement 21. An ophthalmic suspension vehicle is provided that includes a wax dispersion including (a) water; (b) at least one oil; (c) a surfactant; and (d) a wax or wax ester present in a concentration of about 0.5 to about 1.5 weight percent. The wax or wax esters in the ophthalmic suspension vehicle bind a mucin layer, an aqueous layer, and a lipid layer in an eye of a subject and act to maintain or enhance the integrity of an interstitial layer between the mucin layer and the aqueous layer, and interstitial layer between the aqueous layer and the lipid layer.

Statement 22. The present disclosure provides an ophthalmic suspension vehicle of Statement 21, wherein the wax or wax esters act to increase the thickness of the mucin layer, the aqueous layer, the lipid layer, or a combination thereof.

Statement 23. The present disclosure provides an ophthalmic suspension vehicle of any of Statements 21-22, wherein binding and homeostasis enabled by the wax, wax esters or hydrolysis products allows the mucin layer, the aqueous layer and the lipid layer of a tear film to interact with to each other allowing the tear film to remain on the eye for extended periods of time (e.g., at least two hours).

Statement 24. An ophthalmic suspension vehicle is provided that exhibits a zeta potential of from about −60 mV to about −110 mV.

Statement 25. An ophthalmic suspension vehicle is provided that forms a meta stable emulsion which separates into an oil phase and a water phase on contact with an eye and provides lubrication for about 2 to about 12 hours on the eye.

Statement 26. A method for alleviating the symptoms of dry eye is provided which includes the step of contacting an eye with an ophthalmic suspension vehicle of any of Statements 21-25.

Statement 27. The present disclosure provides a method alleviating the symptoms of dry eye of Statement 26, wherein on contact with an eye the ophthalmic suspension vehicle interacts with: a lipid layer; an aqueous layer; a mucin layer; an interface between the lipid layer and the aqueous layer; and an interface between the aqueous layer and the mucin layer of the eye and unprotected corneal cells.

Statement 28. The present disclosure provides a method alleviating the symptoms of dry eye of any of Statements 26-27, where the wax ester of the ophthalmic suspension vehicle is a natural beeswax or a synthetic beeswax.

Statement 29. The present disclosure provides a method alleviating the symptoms of dry eye of any of Statements 26-28, wherein the oil is a mixture of a lighter weight mineral oil and a heavier mineral weight oil.

Statement 30. The present disclosure provides a method alleviating the symptoms of dry eye of any of Statements 26-29, wherein the oil is present in a concentration of about 1.0 weight percent to about 5 weight percent.

Statement 31. The present disclosure provides a method alleviating the symptoms of dry eye of any of Statements 26-30, wherein the surfactant is a mixture of two or more surfactants.

Statement 32. The present disclosure provides a method alleviating the symptoms of dry eye of any of Statements 26-31, wherein (i) the oil is a mixture of a lighter weight oil and a heavier weight oil and is present in a concentration of about 1.0 to about 5.5 weight percent; (ii) the surfactant is a mixture of a Polysorbate 80 in a concentration of about 0.35 to about 0.45 weight percent and a dimyristoylphosphatidylglycerol in a concentration of about 0.3 to about 0.5 weight percent; (iii) the wax ester is a natural or a synthetic beeswax present in a concentration of about 0.5 to about 1.0 weight percent; and the ophthalmic suspension vehicle has an osmolality of about 245 to about 310 mOsmol/kg.

Statement 33. The present disclosure provides a method alleviating the symptoms of dry eye of any of Statements 26-32, wherein the ophthalmic suspension vehicle is packaged in a sterile multi-use or sterile single use container.

Statement 34. The present disclosure provides a method alleviating the symptoms of dry eye of any of Statements 26-33, wherein the ophthalmic suspension vehicle is packaged in a multi-dose non-preserved (MDNP) container or a container including at least one preservative.

Statement 35. The present disclosure provides a method of preparing an ophthalmic suspension vehicle that includes the steps of: (a) preparing a wax ester and a surfactant in a purified or deionized water vehicle; (b) preparing an oil-in-water emulsion comprising an oil in a purified or deionized water vehicle; (c) separately autoclaving the beeswax dispersion and the oil-in-water emulsion; (d) and aseptically blending the autoclaved beeswax dispersion and the oil-in-water emulsion so as to prepare the meta stable oil-in-water emulsion ophthalmic suspension vehicle.

Statement 36. The present disclosure provides a method of preparing an ophthalmic suspension vehicle of Statement 35, wherein the ophthalmic solution provides lubrication for at least about 2 hours on the eye.

Statement 37. The present disclosure provides a method of preparing an ophthalmic suspension vehicle of any of Statements 35-36, wherein the ophthalmic solution provides lubrication for at least about 12 hours on the eye.

Statement 38. The present disclosure provides a method of preparing an ophthalmic suspension vehicle of any of Statements 35-37, wherein on contact with an eye the ophthalmic suspension vehicle penetrates: a lipid layer; an aqueous layer; a mucin layer; an interface between the lipid layer and the aqueous layer; and an interface between the aqueous layer and the mucin layer of the eye and unprotected corneal cells.

Statement 39. The present disclosure provides a method of preparing an ophthalmic suspension vehicle of any of Statements 35-38, wherein the wax ester is a natural beeswax.

Statement 40. The present disclosure provides a method of preparing an ophthalmic suspension vehicle of any of Statements 35-39, wherein the beeswax is a synthetic beeswax Statement 41. The present disclosure provides a method of preparing an ophthalmic suspension vehicle of any of Statements 35-40, wherein the oil is a mixture of a lighter weight oil and a heavier weight oil.

Statement 42. The present disclosure provides a method of preparing an ophthalmic suspension vehicle of any of Statements 35-41, wherein the surfactant is a mixture of two or more surfactants.

Statement 43. The present disclosure provides a method of preparing an ophthalmic suspension vehicle of any of Statements 35-42, wherein (i) the oil is a mixture of a light weight oil and a heavy weight oil and is present in a concentration of about 1.0 to about 5.5 weight percent; (ii) the surfactant is a mixture of a Polysorbate 80 in a concentration of about 0.35 to about 0.45 weight percent and a dimyristoylphosphatidylglycerol in a concentration of about 0.3 to about 0.5 weight percent; (iii) the wax ester is a natural beeswax or a synthetic beeswax present in a concentration of about 0.25 to about 1.0 weight percent; and the ophthalmic suspension vehicle has an osmolality of about 245 to about 310 mOsmol/kg.

Statement 44. The present disclosure provides a method of preparing an ophthalmic suspension vehicle of any of Statements 35-43, wherein the ophthalmic suspension vehicle is packaged in a sterile multi-use or sterile single use container.

Statement 45. The present disclosure provides a method of preparing an ophthalmic suspension vehicle of any of Statements 35-44, wherein the ophthalmic suspension vehicle is packaged in a multi-dose non-preserved (MDNP) container or a container including at least one preservative.

Statement 46. The present disclosure provides a method of preparing an ophthalmic suspension vehicle of any of Statements 35-44, wherein the ophthalmic suspension vehicle is packaged in a container containing a preservative.

Statement 47. The present disclosure provides a method of preparing an ophthalmic suspension vehicle of any of Statements 35-46, wherein the wax esters act to increase the thickness of the mucin layer, the aqueous layer, the lipid layer, or a combination thereof.

Statement 48. The present disclosure provides a method of preparing an ophthalmic suspension vehicle of any of Statements 35-47, wherein binding and homeostasis enabled by the wax esters allows the mucin layer, the aqueous layer and the lipid layer of a tear film to interact with each other allowing the tear film to remain on the eye for at least two hours.

Statement 49. The present disclosure provides a method for delivering at least one pharmaceutical ingredient to a patient in need of treatment comprising administering to an eye of the patient an ophthalmic suspension vehicle that includes at least one wax ester, an anionic polar surfactant and water; and an oil-in-water emulsion comprising at least one oil and water, wherein the ophthalmic suspension vehicle exhibits a mean particle size of at least about 2.0 microns. The ophthalmic suspension vehicle is suited to be combined with at least one pharmaceutical ingredient.

Statement 50. The present disclosure provides a method for delivering at least one pharmaceutical ingredient to a patient in need of treatment of any of Statement 49, wherein the pharmaceutical ingredient is water soluble.

Statement 51. The present disclosure provides a method for delivering at least one pharmaceutical ingredient to a patient in need of treatment of any of Statement s 49-50, wherein the pharmaceutical ingredient is oil soluble.

Statement 52. The present disclosure provides a method for delivering at least one pharmaceutical ingredient to a patient in need of treatment of any of Statement s 49-51, wherein the at least one pharmaceutical ingredient is an antibiotic, antiviral agent, anti-inflammatory agent or antiglaucoma agent.

Statement 53. The present disclosure provides a method for delivering at least one pharmaceutical ingredient to a patient in need of treatment of any of Statement s 49-52, wherein the at least one pharmaceutical ingredient is selected from the group consisting of adenosine diphosphate ribose, antazoline, apraclonidine, apraclonidine, atropine, azelastine, bepotastine, etamethasone, betaxolol, betaxolol, bimatoprost, brimonidine, brinzolamide, bromfenac, bromfenac, cardiolipin peroxidation inhibitors, carteolol, cetrimide, chloramphenicol, ciprofloxacin, cyclosporine, dexamethasone, diclofenac, dorzolamide, emedastine, epinastine, epinastine, flurbiprofen, framycetin sulphate, gentamycin, gramicidin, *hamamelis* water, homatropine, hyaluronic acid, ketotifen fumarate, lacritin/lacritin protein fragment, latanoprost, levobunolol, levofloxacin, lodoxamide loteprednol, lymphocyte function associated antigen 1 (LFA-1) antagonist, modified 19-kDa TNF receptor, moxifloxacin, naphazoline, naphazoline, nedocromil maleate, nicotinic acetylcholine receptor (nAChR) agonist, ofloxacin, olopatadine, pegaptanib, perfluorohexyloctane, pheniramine, pilocarpine, pranoprofen, prednisolone, ranibizumab, reactive aldehyde species inhibitor, recombinant lubricin, rimexolone, sodium, tetracaine, tetrahydrozoline, thiomersal, timolol, tobramycin, trafluprost, travoprost, ketorolac trometamol, trometamol, xylometazoline or any combination thereof.

Statement 54. The present disclosure provides an ophthalmic suspension vehicle for delivery of at least one pharmaceutical ingredient to a patient in need of treatment, the ophthalmic suspension vehicle comprising:
  i) an aqueous phase comprising water and one or more components selected from the group consisting of at least one wax ester, at least one anionic polar surfactant, at least one nonionic surfactant, at least one salt, and at least one phosphate; and
  ii) an oil phase comprising at least one mineral oil and, optionally, at least one wax ester;
  wherein the at least one pharmaceutical ingredient is maintained within the ophthalmic vehicle and in therapeutic contact with the eye for at least two hours after administering to the eye.

Statement 55. The present disclosure provides an ophthalmic suspension vehicle for delivery of at least one pharmaceutical ingredient to a patient in need of treatment of any of Statement 54, wherein the at least one pharmaceutical ingredient is water soluble or oil soluble.

Statement 56. The present disclosure provides an ophthalmic suspension vehicle for delivery of at least one pharmaceutical ingredient to a patient in need of treatment of Statements 54-55, wherein the at least one pharmaceutical ingredient is an antibiotic, antiviral agent, anti-inflammatory agent or antiglaucoma agent.

Statement 57. The present disclosure provides an ophthalmic suspension vehicle for delivery of at least one pharmaceutical ingredient of Statements 54-56, wherein the at least one pharmaceutical ingredient is selected from the group consisting of adenosine diphosphate ribose, antazoline, apraclonidine, apraclonidine, atropine, azelastine, bepotastine, etamethasone, betaxolol, betaxolol, bimatoprost, brimonidine, brinzolamide, bromfenac, bromfenac, cardiolipin peroxidation inhibitors, carteolol, cetrimide, chloramphenicol, ciprofloxacin, cyclosporine, dexamethasone, diclofenac, dorzolamide, emedastine, epinastine, epinastine, flurbiprofen, framycetin sulphate, gentamycin, gramicidin, *hamamelis* water, homatropine, hyaluronic acid, ketotifen fumarate, lacritin/lacritin protein fragment, latanoprost, levobunolol, levofloxacin, lodoxamide loteprednol, lymphocyte function associated antigen 1 (LFA-1) antagonist, modified 19-kDa TNF receptor, moxifloxacin, naphazoline, nedocromil maleate, nicotinic acetylcholine receptor (nAChR) agonist, ofloxacin, olopatadine, pegaptanib, perfluorohexyloctane, pheniramine, pilocarpine, pranoprofen, prednisolone, ranibizumab, reactive aldehyde species inhibitor, recombinant lubricin, rimexolone, sodium, tetracaine, tetrahydrozoline, thiomersal, timolol, tobramycin, trafluprost, travoprost, ketorolac trometamol, trometamol, xylometazoline or any combination thereof.

Statement 58. The present disclosure provides a method for delivering a predetermined amount of at least one pharmaceutical ingredient to a patient in need of treatment, the method comprising the step of:
  administering to an eye of the patient, an ophthalmic suspension comprising:
  a) an ophthalmic suspension vehicle comprising:
    i) an aqueous phase comprising water and one or more components selected from the group consisting of at least one wax ester, at least one anionic polar surfactant, at least one nonionic surfactant, at least one salt, and at least one phosphate; and
    ii) an oil phase comprising at least one mineral oil and, optionally, at least one wax ester; and
  b) at least one pharmaceutical ingredient,
  wherein the at least one pharmaceutical ingredient is maintained within the ophthalmic vehicle and in therapeutic contact with the eye for at least two hours after administering to the eye.

Statement 59. The present disclosure provides a method for delivering at least one pharmaceutical ingredient of Statement 58, wherein the at least one pharmaceutical ingredient is maintained within the ophthalmic suspension vehicle and in therapeutic contact with the eye for up to six hours after administering to the eye.

Statement 60. The present disclosure provides a method for delivering at least one pharmaceutical ingredient of Statements 58-59, wherein the at least one pharmaceutical ingredient is maintained within the ophthalmic suspension vehicle and in therapeutic contact with the eye for at least six hours after administering to the eye.

Statement 61. The present disclosure provides a method for delivering at least one pharmaceutical ingredient of Statements 58-60, wherein the anionic polar surfactant comprises a mixture of a polysorbate non-ionic surfactant at a concentration of about 0.35 to about 0.45 weight percent and an anionic polar dimyristoylphosphatidylglycerol at a concentration of about 0.35 to about 0.55 weight percent.

Statement 62. The present disclosure provides a method for delivering at least one pharmaceutical ingredient of Statements 58-61, wherein the oil phase comprises at least one oil that includes a mixture of a lightweight mineral oil and a heavy weight mineral oil.

Statement 63. The present disclosure provides a method for delivering at least one pharmaceutical ingredient of Statements 58-62, wherein the lightweight mineral oil exhibits a kinetic viscosity of from about 3.0 mm2s-1 to about 34.4 mm2s-1 at 40° C. and the heavy weight mineral oil exhibits a viscosity of kinetic viscosity of from about 34.5 mm2s-1 to about 150 mm2s-1 at 40° C.

Statement 64. The present disclosure provides a method for delivering at least one pharmaceutical ingredient of Statements 58-63, wherein either the oil phase or the aqueous phase comprises at least one wax ester present in a concentration of about 0.8 weight percent to about 1.2 weight percent.

Statement 65. The present disclosure provides a method for delivering at least one pharmaceutical ingredient of Statements 58-64, wherein the at least one wax ester is a natural or synthetic beeswax.

Statement 66. The present disclosure provides a method for delivering at least one pharmaceutical ingredient of Statements 58-65, wherein the ophthalmic suspension exhibits a mean particle size of at least about 2.0 microns to about 20.0 microns.

Statement 67. The present disclosure provides a method for delivering at least one pharmaceutical ingredient of Statements 58-66, wherein the ophthalmic suspension exhibits a mean particle size distribution of from about 5.0 microns to about 15.0 microns.

Statement 68. The present disclosure provides a method for delivering at least one pharmaceutical ingredient of Statements 58-67, wherein the at least one pharmaceutical ingredient is soluble in the aqueous phase.

Statement 69. The present disclosure provides a method for delivering at least one pharmaceutical ingredient of Statements 58-68, wherein the at least one pharmaceutical ingredient is soluble in the oil phase.

Statement 70. The present disclosure provides a method for delivering at least one pharmaceutical ingredient of Statements 58-69, wherein the at least one pharmaceutical ingredient is selected from the group consisting of an antibiotic, antiviral agent, anti-inflammatory agent, anti-allegeric, antiglaucoma agent, dry eye lubricant and ocular gland secretagogue.

Statement 71. The present disclosure provides a method for delivering at least one pharmaceutical ingredient of Statements 58-70, wherein the at least one pharmaceutical ingredient is selected from the group consisting of adenosine diphosphate ribose, antazoline, apraclonidine, apraclonidine, atropine, azelastine, bepotastine, etamethasone, betaxolol, betaxolol, bimatoprost, brimonidine, brinzolamide, bromfenac, bromfenac, cardiolipin peroxidation inhibitors, carteolol, cetrimide, chloramphenicol, ciprofloxacin, cyclosporine, cannabidiol, tetrahydrocannabinol, dexamethasone, diclofenac, dorzolamide, emedastine, epinastine, epinastine, flurbiprofen, framycetin sulphate, gentamycin, gramicidin, *hamamelis* water, homatropine, hyaluronic acid, ketotifen fumarate, lacritin/lacritin protein fragment, latanoprost, levobunolol, levofloxacin, lodoxamide loteprednol, lymphocyte function associated antigen 1 (LFA-1) antagonist, modified 19-kDa TNF receptor, moxifloxacin, naphazoline, naphazoline, nedocromil maleate, nicotinic acetylcholine receptor (nAChR) agonist, ofloxacin, olopatadine, pegaptanib, perfluorohexyloctane, pheniramine, pilocarpine, pranoprofen, prednisolone, ranibizumab, reactive aldehyde species inhibitor, recombinant lubricin, rimexolone, sodium, tetracaine, tetrahydrozoline, thiomersal, timolol, tobramycin, trafluprost, travoprost, ketorolac trometamol, trometamol, and xylometazoline.

Statement 72. An ophthalmic suspension for delivery of at least one pharmaceutical ingredient to a patient in need of treatment, the ophthalmic suspension comprising:
 a) an ophthalmic suspension vehicle comprising:
  i) an aqueous phase comprising water and one or more components selected from the group consisting of at least one wax ester, at least one anionic polar surfactant, at least one nonionic surfactant, at least one salt, and at least one phosphate; and
  ii) an oil phase comprising at least one mineral oil and, optionally, at least one wax ester; and
 b) at least one pharmaceutical ingredient,
 wherein the ophthalmic vehicle exhibits a mean particle size of at least about 2.0 microns.

Statement 73. The present disclosure provides an ophthalmic suspension of Statement 72, wherein the at least one pharmaceutical ingredient is soluble in the aqueous phase.

Statement 74. The present disclosure provides an ophthalmic suspension of Statement 72-73, wherein the at least one pharmaceutical ingredient is soluble in the oil phase.

Statement 75. The present disclosure provides an ophthalmic suspension of Statements 72-74, wherein the at least one pharmaceutical ingredient is selected from the group consisting of an antibiotic, antiviral agent, anti-inflammatory agent, anti-allegeric, antiglaucoma agent, dry eye lubricant and ocular gland secretagogue.

Statement 76. The present disclosure provides an ophthalmic suspension of Statements 72-75, having a negative Zeta potential of from about −60 mV to about −110 mV.

Statement 77. An ophthalmic suspension vehicle for delivery of at least one pharmaceutical ingredient to a patient in need thereof, the ophthalmic suspension vehicle consisting of:
 a wax dispersion comprising natural beeswax particles, an anionic polar surfactant and water;
 sodium hyaluronate; and
 an oil-in-water emulsion comprising an oil and water; and
 optionally, at least one preservative selected from the group consisting of polyhexamethylene biguanide, stabilized oxychloro complex and polyquaternium-1,
 wherein:
 (i) the oil is a mixture of a lighter molecular weight mineral oil and a heavier molecular weight mineral oil and is present in a concentration of about 4.0 to about 6.25 weight percent;
 (ii) the anionic polar surfactant is a mixture of a Polysorbate 80 in a concentration of about 0.35 to about 0.45 weight percent and an anionic polar dimyristoylphosphatidylglyerol in a concentration of about 0.35 to about 0.50 weight percent; and
 (iii) the natural beeswax particles are solid up to about 60° C. and are present in a concentration of about 0.50 to about 1.25 weight percent; and
 wherein the ophthalmic suspension vehicle:
 (i) forms a meta stable emulsion which separates into an oil phase and a water phase on contact with an eye;
 (ii) provides a dwell time on the eye of at least two hours;

(iii) is formulated as a free flowing liquid at room temperature;
(iv) has an osmolality of about 230 mOsmol/kg to about 260 mOsmol/kg; and
(v) has a pH of from about 6.5 to about 7.8.

Statement 78. The present disclosure provides an ophthalmic suspension vehicle of Statement 77, wherein the beeswax is present in a concentration of about 1.0 weight percent.

Statement 79. The present disclosure provides an ophthalmic suspension vehicle of Statements 77-78, wherein the beeswax is Cera Alba or Cera Flava.

Statement 80. The present disclosure provides an ophthalmic suspension vehicle of Statements 77-79, packaged in a sterile single use container.

Statement 81. The present disclosure provides an ophthalmic suspension vehicle of Statements 77-80, packaged in a sterile multi-dose container.

Statement 82. The present disclosure provides a finished pharmaceutical product comprising the ophthalmic suspension vehicle of Statement 77 and a predetermined amount of at least one pharmaceutical ingredient.

Statement 83. The present disclosure provides a finished pharmaceutical product comprising the ophthalmic suspension vehicle of Statement 82, wherein the predetermined amount of the at least one pharmaceutical ingredient is a therapeutically effective dose.

Statement 84. The present disclosure provides a finished pharmaceutical product comprising the ophthalmic suspension vehicle of Statement 82, wherein the predetermined amount of the at least one pharmaceutical ingredient is a sub-therapeutically effective dose.

What is claimed is:

1. An ophthalmic suspension for delivery of at least one pharmaceutical ingredient to a patient in need thereof, the ophthalmic suspension comprising:
    a) an ophthalmic suspension vehicle comprising:
        i) an aqueous phase comprising water and one or more components selected from the group consisting of a wax ester, an anionic polar surfactant, an nonionic surfactant, a salt and a phosphate; and
        ii) an oil phase comprising at least one mineral oil and, optionally, at least one wax ester; and
    b) at least one pharmaceutical ingredient,
    wherein the ophthalmic suspension vehicle has an osmolality of from about 270 mOsmol/kg to about 315 mOsmol/kg, a zeta potential of from about −60 mV to about −110 mV, and an ionic mobility of from about −6 (μm/s)/(V/cm) to about −7.5 (μm/s)/(V/cm).

2. The ophthalmic suspension of claim 1, wherein the at least one pharmaceutical ingredient is soluble in the aqueous phase.

3. The ophthalmic suspension of claim 1, wherein the at least one pharmaceutical ingredient is soluble in the oil phase.

4. The ophthalmic suspension of claim 1, wherein the at least one pharmaceutical ingredient is selected from the group consisting of an antibiotic, antiviral agent, anti-inflammatory agent, anti-allegeric, antiglaucoma agent, dry eye lubricant, and ocular gland secretagogue.

5. The ophthalmic suspension of claim 1, having a negative zeta potential of from about −75 mV to about −95 mV.

6. The ophthalmic suspension of claim 1, wherein the at least one pharmaceutical ingredient is present in a predetermined amount.

7. The ophthalmic suspension of claim 6, wherein the predetermined amount is a therapeutically effective dose.

8. The ophthalmic suspension of claim 6, wherein the predetermined amount is a sub-therapeutically effective dose.

9. The ophthalmic suspension of claim 1, wherein the ophthalmic suspension vehicle has an osmolality of from about 270 mOsmol/kg to about 300 mOsmol/kg.

10. A method for delivering a predetermined amount of at least one pharmaceutical ingredient to a patient in need of treatment, the method comprising the step of:
    administering to an eye of the patient, an ophthalmic suspension comprising:
    a) an ophthalmic suspension vehicle comprising:
        i) an aqueous phase comprising water and one or more components selected from the group consisting of at least one wax ester, at least one anionic polar surfactant, at least one nonionic surfactant, at least one salt, and at least one phosphate; and
        ii) an oil phase comprising at least one mineral oil and, optionally, at least one wax ester; and
    b) at least one pharmaceutical ingredient,
    wherein the ophthalmic suspension exhibits a zeta potential of from about −60 mV to about −110 mV and an ionic mobility of from about −5.9 (μm/s)/(V/cm) to about −7.4 (μm/s)/(V/cm).

11. The method of claim 10, wherein the ophthalmic suspension vehicle has an osmolality of from about 270 mOsmol/kg to about 315 mOsmol/kg.

12. The method of claim 10, wherein the at least one pharmaceutical ingredient is maintained within the ophthalmic suspension vehicle and in therapeutic contact with the eye for at least six hours after administering to the eye.

13. The method of claim 10, wherein the at least one pharmaceutical ingredient is soluble in the aqueous phase.

14. The method of claim 10, wherein the at least one pharmaceutical ingredient is soluble in the oil phase.

15. A method of increasing lipid layer thickness on a patient's eye in need of treatment, the method comprising the step of:
    administering to an eye of the patient, an ophthalmic suspension comprising:
    a) an ophthalmic suspension vehicle comprising:
        i) an aqueous phase comprising water and one or more components selected from the group consisting of at least one wax ester, at least one anionic polar surfactant, at least one nonionic surfactant, at least one salt, and at least one phosphate; and
        ii) an oil phase comprising at least one mineral oil and, optionally, at least one wax ester; and
    b) at least one pharmaceutical ingredient,
    wherein the ophthalmic suspension exhibits a zeta potential of from about −60 mV to about −110 mV and an ionic mobility of from about −5.9 (μm/s)/(V/cm) to about −7.4 (μm/s)/(V/cm).

16. The method of claim 15, wherein the lipid layer thickness is increased by at least 20 nm at four hours after administration.

17. The method of claim 15, wherein the at least one pharmaceutical ingredient is maintained within the ophthalmic suspension vehicle and in therapeutic contact with the eye for at least six hours after administering to the eye.

18. The method of claim 15, wherein the at least one pharmaceutical ingredient is soluble in the aqueous phase.

19. The method of claim 15, wherein the at least one pharmaceutical ingredient is soluble in the oil phase.

20. The method of claim 15, wherein the ophthalmic suspension vehicle has an osmolality of from about 270 mOsmol/kg to about 315 mOsmol/kg.

\* \* \* \* \*